(12) United States Patent
Gilligan

(10) Patent No.: US 7,144,894 B2
(45) Date of Patent: Dec. 5, 2006

(54) SULFONAMIDE BICYCLIC COMPOUNDS

(75) Inventor: Paul J. Gilligan, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 59 days.

(21) Appl. No.: 11/231,410

(22) Filed: Sep. 21, 2005

(65) Prior Publication Data

US 2006/0063799 A1    Mar. 23, 2006

Related U.S. Application Data

(60) Provisional application No. 60/612,424, filed on Sep. 23, 2004.

(51) Int. Cl.
  *C07D 209/36*   (2006.01)
  *C07D 217/22*   (2006.01)
  *A61K 31/47*   (2006.01)
  *A61K 31/404*   (2006.01)

(52) U.S. Cl. ...................... 514/309; 514/312; 514/414; 514/415; 546/141; 546/153; 548/484

(58) Field of Classification Search ................ 546/141, 546/153; 514/309, 312, 414, 415; 548/484
See application file for complete search history.

(56) References Cited

U.S. PATENT DOCUMENTS

2004/0127494 A1  7/2004  Parker et al.

*Primary Examiner*—Zinna N. Davis
(74) *Attorney, Agent, or Firm*—James Epperson

(57) ABSTRACT

The invention encompasses compounds of Formula I, including pharmaceutically acceptable salts and solvates, their pharmaceutical compositions, and their uses in inhibiting β-amyloid peptide (β-AP) production

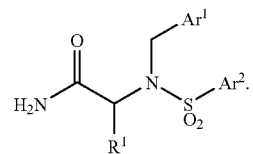

16 Claims, No Drawings

SULFONAMIDE BICYCLIC COMPOUNDS

REFERENCE TO RELATED APPLICATIONS

This application claims the benefit of U.S. Provisional Application Ser. No. 60/612,424 filed Sep. 23, 2004.

BACKGROUND OF THE INVENTION

Alzheimer's Disease is a progressive, neurodegenerative disorder characterized by memory impairment and cognitive dysfunction. Alzheimer's Disease is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (greater than $100 billion annually in the U.S.) and includes the suffering of the patients, the suffering of families, and the lost productivity of patients and caregivers. As the longevity of society increases, the occurrence of Alzheimer's disease will markedly increase. It is estimated that more than 10 million Americans will suffer from Alzheimer's disease by the year 2020, if methods for prevention and treatment are not found. Currently, Alzheimer's disease is estimated to afflict 10% of the population over age 65 and up to 50% of those over the age of 85. There is currently no effective treatment.

There have been many theories relating to the etiology and pathogenesis of Alzheimer's disease. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of Alzheimer's disease and related disorders strongly supports the amyloidogenic theories.

The β-amyloid precursor protein (β-APP), a large membrane spanning glycoprotein found in tissues of mammals, including humans, is encoded by a gene on the long arm of human chromosome 21. The main constituent of the plaques, tangles and amyloid deposits is known to be β-amyloid peptides (β-AP), composed of approximately 39 to 43 amino acid fragments of β-APP, and in particular, the 40 amino acid fragment known as Aβ1-40. Several lines of evidence support the involvement of β-AP in the pathogenesis of Alzheimer's disease lesions. β-AP and related fragments have been shown to be toxic for PC-12 cell lines and primary cultures of neurons, as well as causing neuronal degeneration with accompanying amnesia in rodents. Strong evidence for the role of β-AP in Alzheimer's disease consists of observations of genetic β-APP mutations in individuals with certain forms of Familial Alzheimer's Disease (FAD) and the correlation of disease onset with altered release of β-AP fragments.

It is presently believed that the development of amyloid plaques in the brains of Alzheimer's disease patients is a result of excess production and/or reduced clearance or removal of β-AP. It is known that a basal level of β-AP production may be a normal process and that multiple pathways for cleavage of β-APP exist. Currently, however, it is unclear which classes of proteinases or inhibitors thereof that would be effective in treating Alzheimer's disease. Various peptidergic compounds and their pharmaceutical compositions have been disclosed as useful in inhibiting or preventing amyloid protein deposits in brains of Alzheimer's disease and Down's Syndrome patients.

N-benzenesulfonamido-1-(substituted)glycineamides have been disclosed. See Parker, M. F. et al., PCT application WO 03/053912, published Jul. 3, 2003. Nothing in this reference teaches or suggests the novel compounds of this invention.

DESCRIPTION OF THE INVENTION

The invention encompasses compounds of Formula I, including pharmaceutically acceptable salts and solvates, their pharmaceutical compositions, and their uses in inhibiting β-amyloid peptide (β-AP) production.

One aspect of the invention are compounds of Formula I

[Structure of Formula I: $H_2N$-C(=O)-CH($R^1$)-N($CH_2Ar^1$)-S(=O)$_2$-$Ar^2$]

I wherein:

$Ar^1$ is [indoline with $R^2$ on N], [indole with $R^3$ at 2-position and $R^2$ on N], [isoquinolinone with $R^2$ on N], or [tetrahydroquinoline with O and $R^2$ on N];

$Ar^2$ is [phenyl with $R^5$ and $R^6$ substituents] or [thiophene with $R^6$ substituent];

$R^1$ is $C_{1-6}$alkyl, $(C_{3-7}$cycloalkyl$)C_{1-6}$alkyl, or $C_{1-6}$fluoroalkyl;

$R^2$ is hydrogen, $C_{1-6}$alkyl, $(C_{3-7}$cycloalkyl$)C_{1-6}$alkyl, (phenyl)$C_{1-6}$alkyl, (pyridinyl)$C_{1-6}$alkyl, $(C_{1-6}$alkoxy$)C_{1-6}$alkyl, $COR^4$, or $CO_2R^4$;

$R^3$ is hydrogen or $C_{1-6}$alkyl;

$R^4$ is $C_{1-6}$alkyl, or $C_{3-7}$cycloalkyl;

$R^5$ is halogen; and $R^6$ is hydrogen or halogen;

or a pharmaceutically acceptable salt of solvate thereof.

Another aspect of the invention are compounds of Formula I where $Ar^1$ is

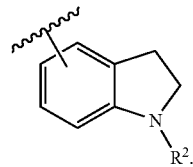

Another aspect of the invention are compounds of Formula I where $Ar^1$ is

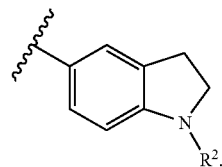

Another aspect of the invention are compounds of Formula I where $Ar^1$ is

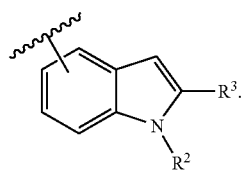

Another aspect of the invention are compounds of Formula I where $Ar^1$ is

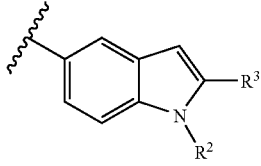

and $R^3$ is hydrogen or methyl.

Another aspect of the invention are compounds of Formula I where $Ar^1$ is

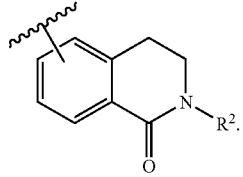

Another aspect of the invention are compounds of Formula I where $Ar^1$ is

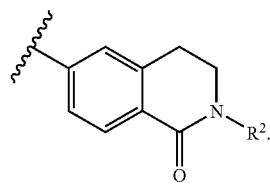

Another aspect of the invention are compounds of Formula I where $Ar^1$ is

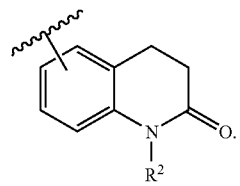

Another aspect of the invention are compounds of Formula I where $Ar^1$ is

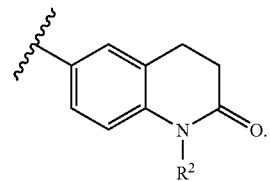

Another aspect of the invention are compounds of Formula I where $Ar^2$ is 4-chlorophenyl.

Another aspect of the invention are compounds of Formula I where $R^2$ is selected from the group consisting of n-propyl, i-propyl, n-butyl, s-butyl, i-butyl, t-butyl, difluoroethyl, trifluoropropyl, and cyclopropylmethyl.

Another aspect of the invention are compounds of Formula I where $R^2$ is selected from the group consisting of hydrogen, methyl, ethyl, n-propyl, i-propyl, n-butyl, s-butyl, i-butyl, t-butyl, cyclopropylmethyl, cyclobutylmethyl, methoxyethyl, cyclopentylcarbonyl, butyloxycarbonyl, benzyl, and pyridinylmethyl.

Another aspect of the invention are compounds of Formula I where $R^3$ is hydrogen or methyl.

Another aspect of the invention are compounds of Formula Ia.

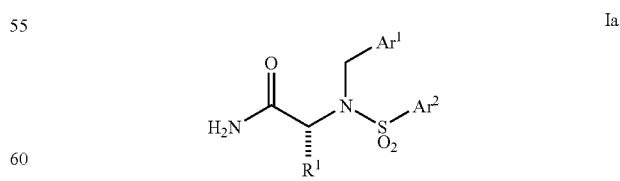

"Alkyl" and terms containing substituted alkyl moieties include all straight and branched chain configurations. "Fluoroalkyl" means an alkyl group where at least one hydrogen atom is replaced with fluorine and up to all hydrogen atoms are replaced with fluorine, from monofluoroalkyl to perfluoroalkyl. "Aryl" includes both carbocyclic and heterocyclic aromatic ring systems.

Compounds of Formula I include all pharmaceutically acceptable salt forms. Pharmaceutically acceptable salts are those in which the counter ions do not contribute significantly to the physiological activity or toxicity of the compounds and as such function as pharmacological equivalents. The salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Compounds of Formula I include all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate. Some hydrated forms include monohydrate, hemihydrate, and dihydrate.

Some compounds of Formula I may contain asymmetric carbon atoms, an example of which is shown below. Compounds of Formula I include all stereoisomeric forms, both separated isomers and mixtures thereof. Stereoisomers can be separated by methods known in the art.

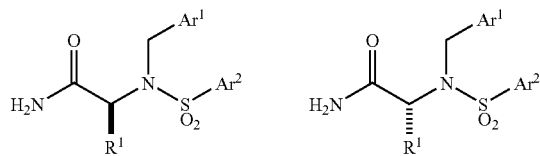

Some compounds of the invention are
2R-(N-1-t-butyloxycarbonylindol-5-ylmethyl-N-4-chlorophenylsulfonylamino)-4-methyl-pentanamide;
2R-(N-indol-5-ylmethyl-N-4-chlorophenylsulfonyl)amino-4-methyl-pentanamide;
2R-(1-t-Butyloxycarbonyl-2-methylindol-5-ylmethylamino)-4-methyl-pentanamide;
2R-(N-(1-t-Butyloxycarbonyl-2-methylindol-5-ylmethyl)-N-4-chlorophenylsulfonyl)amino-4-methyl-pentanamide;
2R-(N-(2-methylindol-5-ylmethyl)-N-4-chlorophenylsulfonyl)amino-4-methyl-pentanamide;
2R-(N-(1-oxo-1,2,3,4-tetrahydroisoquinolin-6-ylmethyl)-N-4-chlorophenylsulfonyl)amino-4-methyl-pentanamide;
2R-(N-(1-oxo-2-ethyl-1,2,3,4-tetrahydroisoquinolin-6-ylmethylamino)-N-4-chlorophenylsulfonyl)amino-4-methyl-pentanamide;
2R-(N-(2-oxo-1,2,3,4-tetrahydroquinolin-6-ylmethyl)-N-4-chlorophenylsulfonyl)amino-4-methyl-pentanamide;
2R-(N-1-t-Butyloxycarbonylindolin-5-yl-N-4-chlorophenylsulfonyl)methylamino-4-methyl-pentanamide;
2R-(N-indolin-5-yl-N-4-chlorophenylsulfonyl)methylamino-4-methyl-pentanamide;
2R-(N-1-methylindolin-5-yl-N-4-chlorophenylsulfonyl)methylamino-4-methyl-pentanamide;
2R-(N-1-butylindolin-5-yl-N-4-chlorophenylsulfonyl)methylamino-4-methyl-pentanamide;
2R-(N-1-cyclopentylcarbonylindolin-5-yl-N-4-chlorophenylsulfonyl)methylamino-4-methyl-pentanamide;
2R-(N-(1-oxo-2-methyl-1,2,3,4-tetrahydroisoquinolin-6-ylmethylamino)-N-4-chlorophenylsulfonyl)amino-4-methyl-pentanamide;
2R-(N-(1-oxo-2-propyl-1,2,3,4-tetrahydroisoquinolin-6-ylmethylamino)-N-4-chlorophenylsulfonyl)amino-4-methyl-pentanamide;
2R-(N-(1-oxo-2-butyl-1,2,3,4-tetrahydroisoquinolin-6-ylmethylamino)-N-4-chlorophenylsulfonyl)amino-4-methyl-pentanamide;
2R-(N-(1-oxo-2-benzyl-1,2,3,4-tetrahydroisoquinolin-6-ylmethylamino)-N-4-chlorophenylsulfonyl)amino-4-methyl-pentanamide;
2R-(N-(1-oxo-2-(2-methoxyethyl)-1,2,3,4-tetrahydroisoquinolin-6-ylmethylamino)-N-4-chlorophenylsulfonyl)amino-4-methyl-pentanamide;
2R-(N-(1-oxo-2-cyclopropylmethyl-1,2,3,4-tetrahydroisoquinolin-6-ylmethylamino)-N-4-chlorophenylsulfonyl)amino-4-methyl-pentanamide;
2R-(N-(1-oxo-2-cyclobutylmethyl-1,2,3,4-tetrahydroisoquinolin-6-ylmethylamino)-N-4-chlorophenylsulfonyl)amino-4-methyl-pentanamide;
2R-(N-(1-oxo-2-(2-pyridylmethyl)-1,2,3,4-tetrahydroisoquinolin-6-ylmethylamino)-N-4-chlorophenylsulfonyl)amino-4-methyl-pentanamide;
2R-(N-(1-oxo-2-ethyl-1,2,3,4-tetrahydroisoquinolin-6-ylmethylamino)-N-4-chlorophenylsulfonyl)amino-3-cyclopropyl-propanamide;
2R-(N-(1-oxo-2-ethyl-1,2,3,4-tetrahydroisoquinolin-6-ylmethylamino)-N-4-chlorophenylsulfonyl)amino-4,4-difluorobutanamide;
2R-(N-(1-oxo-2-(2-propyl)-1,2,3,4-tetrahydroisoquinolin-6-ylmethylamino)-N-4-chlorophenylsulfonyl)amino-3-cyclopropyl-propanamide; and
2R-(N-(1-oxo-2-(3-pentyl)-1,2,3,4-tetrahydroisoquinolin-6-ylmethylamino)-N-4-chlorophenylsulfonyl)amino-3-cyclopropyl-propanamide.

Synthetic Methods

Compounds of Formula I can be made according to methods known in the art including those described and illustrated in the schemes below. The formulas and variables illustrated in the synthetic methods section are intended only to assist describing the synthesis of Formula I compounds and are not to be confused with the variables used to define Formula I compounds in the claims or in other sections of the specification.

Some Formula I compounds can be prepared by the methods illustrated in Scheme 1. Compounds of Formula 2 can be reacted with sulfonylating agents $R^3SO_2Cl$ under appropriate conditions to generate compounds of Formula 3. Formula 3 compounds can be reacted with alkylating agents to generate compounds of Formula 1. Compounds of Formula 3 can also be reacted with alcohols of formula $HO(CH^2)_mR^4$ in the presence of a dialkyl azodicarboxylate and a triaryl phosphine to provide compounds of Formula 1. Compounds of Formula 2 can be reductively alkylated with aldehydes of formula $OHC(CH_2)_{m-1}R^4$ in the presence of a reducing agent to provide compounds of Formula 4. Compounds of Formula 4 can be reacted with sulfonylating agents of formula $R^3SO_2Cl$ to generate compounds of Formula 1.

Scheme 1.

Equation 1:

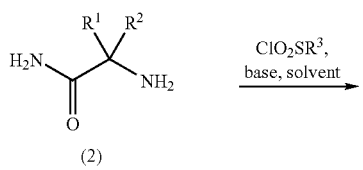

Equation 2:

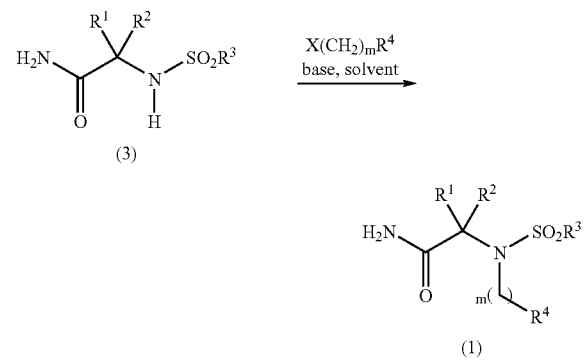

Equation 3:

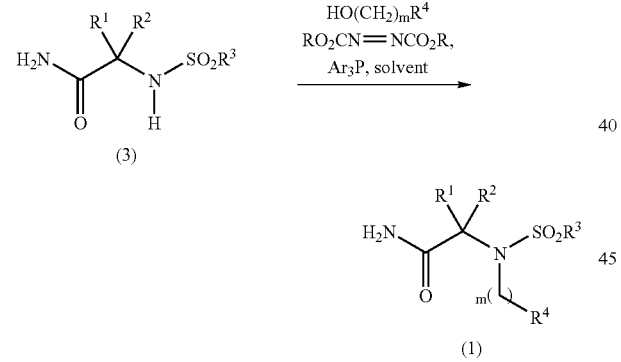

Equation 4:

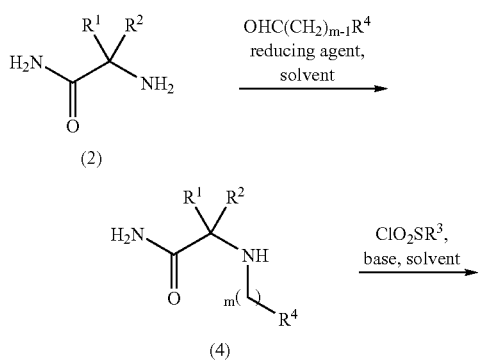

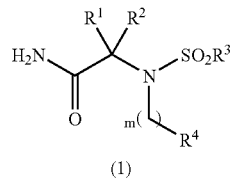

Some Formula I compounds can be prepared by the methods illustrated in Scheme 2. Formula 6 compounds can be reacted with sulfonylating agents of formula $R^3SO_2Cl$ to generate compounds of Formula 7. Formula 7 compounds can be reacted with alkylating agents to generate compounds of Formula 9. Compounds of Formula 7 can also be reacted with alcohols of formula $HO(CH_2)_mR^4$ in the presence of a dialkyl azodicarboxylate and a triaryl phosphine to provide compounds of Formula 9. Compounds of Formula 6 can be reductively alkylated with aldehydes of formula $OHC(CH^2)_{m-1}R^4$ to provide compounds of Formula 8. Compounds of Formula 8 can be reacted with sulfonylating agents of formula $R_3SO_2Cl$ to generate compounds of Formula 9. Esters of Formula 9 can be converted to carboxylic acids of Formula 10 by treatment with acid or base. Acids of Formula 9 can be converted to amides of Formula 1 by treatment with $NH_4Cl$ or $NH_3$ in the presence of a coupling reagent and a base.

Scheme 2.

Equation 1

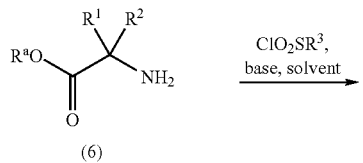

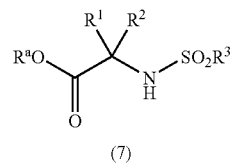

Equation 2

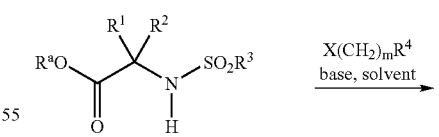

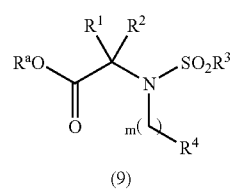

Equation 3

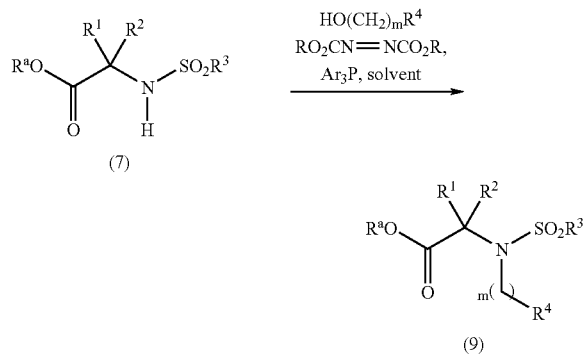

Equation 4

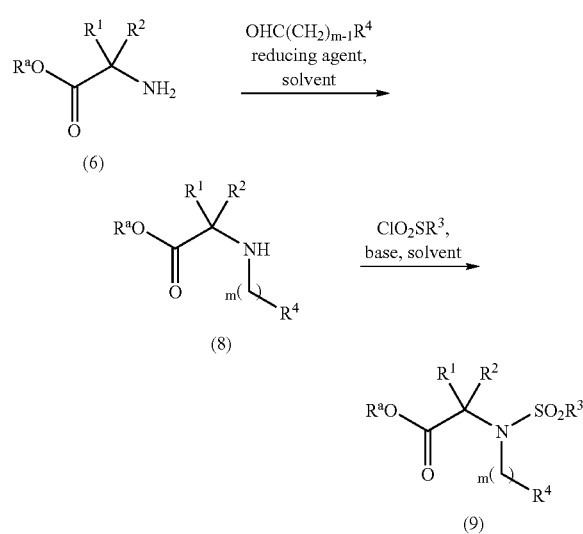

Equation 5

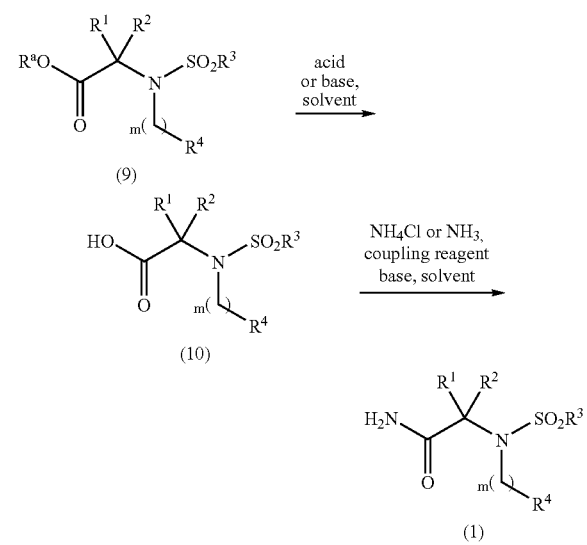

Biological Methods

Competitive in vitro binding assays can be used to identify compounds that inhibit γ-secretase activity. For example, [³H]-Compound A can be used for binding assays with membranes from THP-1 cells (Seiffert, D. et al., *J. Biol. Chem.* 2000, 275, 34086). Compound A is described in U.S. patent U.S. Pat. No. 6,331,408; PCT Publication WO 00/28331; PCT Publication WO 00/07995; and *J. Biol. Chem.* 2000, 275, 34086.

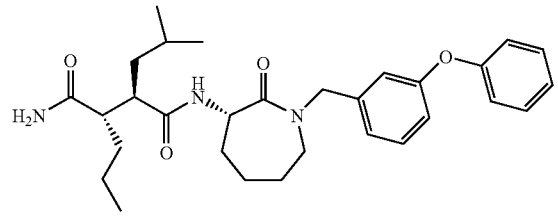

Compound A

To evaluate compounds using this assay, THP-1 cells were grown in spinner cultures in RPMI 1640 containing L-glutamine and 10 μM β-mercaptoethanol to a density of $5 \times 10^5$ cells/ml. Cells were harvested by centrifugation and cell pellets were quick frozen in dry ice/ethanol and stored at −70° C. prior to use. The pellets of approximately $2 \times 10^4$ THP-1 cells were homogenized using a Brinkman Polytron at setting 6 for 10 sec. The homogenate was centrifuged at 48,000×g for 12 min, and the resulting pellet was washed by repeating the homogenization and centrifugation. The final cell pellet was resuspended in buffer to yield a protein concentration of approximately 0.5 mg/ml. Assays were initiated by the addition of 150 μl of membrane suspension to 150 μl of assay buffer containing 0.064 μCi of radioligand and various concentrations of unlabeled compounds. Binding assays were performed in duplicate in polypropylene 96-well plates in a final volume of 0.3 ml containing 50 mM Hepes, pH 7.0, and 5% dimethyl sulfoxide. Nonspecific binding was defined using incubations with 300 nM compound A (Seiffert, D. et al., *J. Biol. Chem.* 2000, 275, 34086). After incubating at 23° C. for 1.3 hr, bound ligand was separated from free radioligand by filtration over GFF glass fiber filters presoaked in 0.3% ethyleneimine polymer solution. Filters were washed three times with 0.3 ml of ice cold phosphate-buffered saline, pH 7.0, containing 0.1% Triton X-100. Filter-bound radioactivity was measured by scintillation counting. $IC_{50}$ values were then determined and used to calculate $K_i$ values using the Cheng-Prusoft correction for $IC_{50}$ values. Compounds were scored as active γ-secretase inhibitors if $K_i$ values were less than 10 μM.

γ-Secretase inhibitors were also evaluated using in vitro assays based on the inhibition of Aβ formation in cultured cells. Cultured human cell lines, such as HEK293 and H4 cells, which express APP and γ-secretase activity or transfected derivative cell lines that overexpress wild-type APP, mutant APP, or APP fusion proteins will secrete Aβ peptides into the culture media that can be quantified as previously outlined (Dovey H. et al., *J. Neurochem.* 2001, 76, 173). The incubation of these cultured cells with γ-secretase inhibitors decreases the production of Aβ peptides. For instance, H4 cells stably transfected to overexpress the HPLAP-APP fusion protein described above were grown as above, detached, and adjusted to 2×105 cells/ml. 100 μl of the resulting suspension was then added to each well of a 96-well plate. After 4 hrs, the media was removed and replaced with 100 μl serum-free media containing various dilutions of the test compound. Plates were then incubated for 18 hrs at 37° C. and a 100 μl aliquot of the tissue culture supernatant was removed for determination of Aβ levels using time-resolved fluorescence of the homogenous sample as outlined above. The extent of Aβ inhibition was used to calculate the $IC_{50}$ value for the test compound. Compounds are considered active when tested in the above assay if the $IC_{50}$ value for the test compound is less than 50 μM.

Representative compounds were evaluated in the above assay and were determined to inhibit Aβ formation. Results are summarized in Table 2.

TABLE 1

Inhibition of β-amyloid peptide formation in human H4 cells.

| Example | Binding affinity ($IC_{50}$ in nM) |
|---|---|
| 2 | +++ |
| 3 | +++ |
| 4 | +++ |
| 5 | +++ |
| 6 | +++ |
| 7 | ++ |
| 9 | +++ |
| 10 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |

Activity ($IC_{50}$): 0.25–50 nM = +++; 50–500 nM = ++; 500–10000 nM = +.

In addition to cleaving APP, γ-secretase cleaves other substrates. These include the Notch family of transmembrane receptors (see Selkoe, D. *Physiol. Rev.* 2001, 81, 741; Wolfe, M. *J. Med. Chem.* 2001, 44, 2039); LDL receptor-related protein (May, P. et. al. *J. Biol. Chem.* 2002, 277, 18736); ErbB-4 (N[1], C. Y. et al. *Science* 2001, 294, 2179); E-cadherin (Marambaud, P. et al., *EMBO J.* 2002, 21, 1948); and CD44 (Okamoto, I., *J. Cell Biol.* 2001, 155, 755). If inhibition of cleavage of non-APP substrates causes undesirable effects in humans, then desired γ-secretase inhibitors would preferentially inhibit APP cleavage relative to unwanted substrates. Notch cleavage can be monitored directly by measuring the amount of cleavage product or indirectly by measuring the effect of the cleavage product on transcription (Mizutani, T. et. al. *Proc. Natl. Acad. Sci. USA* 2001, 98, 9026).

Pharmaceutical Composition and Methods of Use

Another aspect of this invention includes pharmaceutical compositions comprising at least one compound of Formula I in combination with at least one pharmaceutical adjuvant, carrier, or diluent.

Another aspect of this invention relates to a method of treatment of disorders characterized by aberrant extracellular deposition of amyloid and which are responsive to the inhibition of β-amyloid peptide in a patient in need thereof, which comprises administering a therapeutically effective amount of a compound of Formula I or a nontoxic pharmaceutically acceptable salt or solvate thereof.

Another aspect of this invention relates to a method for treating systemic (vascular) amyloidosis, pulmonary or muscle amyloidosis, Alzheimer's Disease, Down's Syndrome, or other diseases characterized by extracellular amyloid deposition in a patient in need thereof, which comprises administering a therapeutically effective amount of a compound of Formula I or a non-toxic pharmaceutically acceptable salt or solvate thereof.

The compounds are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10, mg, 100, mg, 250 mg, 500 mg, and 1000 mg. Liquid compositions are generally in a unit dosage range of 1–100 mg/mL. Some examples of liquid dosage units are 1 mg/mL, 10 mg/mL, 25, mg/mL, 50 mg/mL, and 100 mg/mL.

The invention encompasses all conventional modes of administration; oral and parenteral methods are preferred. Typically, the daily dose will be 0.01–100 mg/kg body weight daily. Generally, more compound is required orally and less parenterally. The specific dosing regime, however, should be determined by a physician using sound medical judgement.

DESCRIPTION OF SPECIFIC EMBODIMENTS

Analytical data were generated using the following procedures. Proton NMR spectra were recorded on an Varian FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using electrospray ionization (ES, + or −) or atmospheric chemiionization (APCI, + or −) with $NH_3$ as the carrier gas) or gas chromatography on a Hewlett Packard 5988A model spectrometer. Melting points were recorded on a Buchi Model 510 melting point apparatus and are uncorrected. Boiling points are uncorrected. All pH determinations during workup were made with indicator paper. Combustion analyses were performed by Quantitative Technologies, Whitehouse, N.J.

Reagents were purchased from commercial sources and, where necessary, purified prior to use. Chromatography (thin layer (TLC) or preparative) was performed on silica gel 60 using the solvent systems indicated below. For mixed solvent systems, the volume ratios are given. Otherwise, parts and percentages are by weight.

The following abbreviations are used below: DMF (N,N-dimethylformamide), THF (tetrahydrofuran), EtOAc (ethyl acetate), HOAc (acetic acid), DCE (1,2-dichloroethane), DCM (dichloromethane), TFA (trifluoroacetic acid).

Intermediate 1

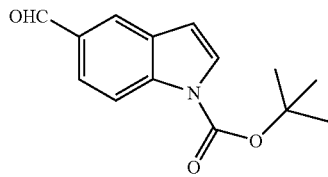

1-(t-Butyloxycarbonyl)-5-formylindole. 5-Formylindole (1.45 g, 10.0 mmol) and 4-dimethylaminopyridine (1.47 g, 12.0 mmol) were dissolved in acetonitrile (20 mL) with stirring at ambient temperature. Once dissolution was complete, the reaction mixture was cooled to −10° C. with stirring. Di-t-butylcarbonate (2.18 g, 10.0 mmol) was added in one portion. Stirring was continued for 2 h. The reaction mixture was diluted with EtOAc (50 mL) and the organic solution was washed successively with water (20 mL), a 1N HCl solution (10 mL), a saturated NaHCO$_3$ solution (20 mL) and brine (20 mL). The organic solution was dried over MgSO$_4$ and filtered. Solvent was removed in vacuo from the filtrate to provide a pale yellow oil (2.45 g, 100% yield): $^1$H NMR (CDCl$_3$, 300 MHz): 10.1 (s, 1H), 8.31 (d, 1H, J=8), 8.12 (s, 1H), 7.87 (dd, 1H, J=8, 1), 7.70 (d, 1H, J=4), 6.71 (d, 1H, J=4), 1.71 (s, 9H).

Intermediate 2

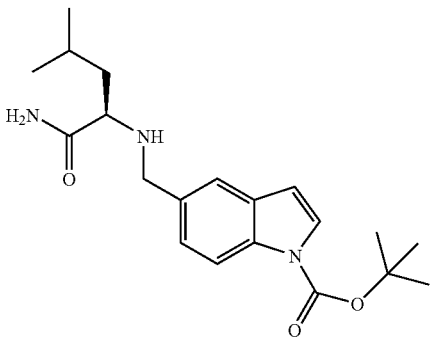

2R-(1-t-Butyloxycarbonylindol-5-ylmethylamino)-4-methyl-pentanamide. D-Leucinamide (1.0 g, 6.0 mmol), 1-(t-butyloxycarbonyl)-5-formylindole (Example 1, 1.23 g, 5.0 mmol) and DCE (15 mL) were mixed at room temperature. Sodium triacetoxyborohydride (1.48 g, 7.0 mmol) was added in one portion with vigorous stirring. After 2 h, another portion (0.15 g, 0.7 mmol) was added and stirring was continued for an additional 6 h. The reaction mixture was diluted with a saturated NaHCO$_3$ solution (10 mL). Three extractions with EtOAc, washing the combined organic layers with brine, drying over Na$_2$SO$_4$ and filtration provided a solution. Removal of solvent in vacuo afforded an oil. Column chromatography (DCM:MeOH:95:5) provided three fractions, after removal of solvent in vacuo: (1) 1-(t-Butyloxycarbonyl)-5-hydroxymethylindole (162 mg, 11% yield, Rf=0.5): $^1$H NMR (CDCl$_3$, 300 MHz): 8.11 (d, 1H, J=8), 7.61 (d, 1H, J=2), 7.54 (s, 1H), 7.31 (dd, 1H, J=8,2), 6.55 (d, 1H, J=3), 4.75 (s, 2H), 1.69 (s, 9H); (2) 2R-bis-(1-t-butyloxycarbonylindol-5-ylmethyl)amino-4-methylpentanamide BMS594447 (382 mg, 12% yield, R$_f$=0.4): $^1$H NMR (CDCl$_3$, 300 MHz): 8.1 (d, 2H, J=8), 7.61 (d, 2H, J=2), 7.52 (s, 2H), 7.31 (dd, 2H, J=8,2), 6.62 (m, 1H), 6.56 (d, 2H, J=4), 6.05 (br s, 1H), 3.85 (d, 2H, J=16), 3.66 (d, 2H, J=16), 3.35 (m, 1H), 1.69 (s, 18H), 0.96 (d, 3H, J=7), 0.87 (d, 3H, J=7); MS (ES+): 589.4 (C35H45N3O5) and (3) the title product (986 mg, 55% yield, R$_f$=0.3): $^1$H NMR (CDCl$_3$, 300 MHz): 8.10 (d, 1H, J=8), 7.61 (d, 1H, J=2), 7.49 (d, 1H, J=1), 7.28–7.20 (m, 3H), 6.55 (d, 1H, J=4), 3.93 (d, 1H, J=16), 3.77 (d, 1H, J=16), 3.28–3.20 (m, 1H), 1.69 (s, 9H), 0.94 (d, 3H, J=7), 0.85 (d, 3H, J=7); MS (ES+): 360 (C$_{20}$H$_{30}$N$_3$O$_3$, M++H).

Intermediate 3

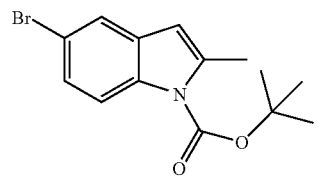

5-Bromo-2-methyl-1-t-butyloxycarbonylindole. 5-Bromo-2-methylindole (4.2 g, 200.0 mmol), di-t-butylcarbonate (4.37 g, 20 mmol), 4-dimethylaminopyridine (2.93 g, 24 mmol) and CH$_3$CN (50 mL) were mixed and stirred at room temperature for 16 h. The reaction mixture was diluted with EtOAc (300 mL) and the organic solution was washed successively with water (50 mL), a 1N HCl solution (50 mL), a saturated NaHCO$_3$ solution (2×50 mL) and brine (25 mL). The organic layer was dried over MgSO$_4$, filtered and concentrated in vacuo to afford an oil (6.11 g, 99% yield): $^1$H NMR (CDCl$_3$, 300 MHz): 7.98 (d, 1H, J=9), 7.56 (d, 1H, J=1), 7.32 (dd, H, J=9, 1), 6.27 (s, 1H), 2.60 (d, 3H, J=1), 1.69 (s, 9H).

Intermediate 4

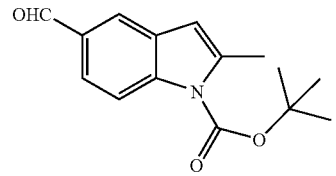

5-Formyl-2-methyl-1-t-butyloxycarbonylindole. A solution of 5-bromo-2-methyl-1-t-butyloxycarbonylindole (1.55 g, 5.0 mmol) and DMF (0.39 mL, 5.0 mmol) in anhydrous THF (15 mL) was cooled with stirring to −78° C. A solution of t-butyl lithium in heptane (1.7M, 7.35 mL, 12.5 mmol) was added dropwise over 5 min. The reaction mixture was then stirred for 1 h. HOAc (1 mL) was added and the reaction mixture was diluted with EtOAc (50 mL). The organic mix was washed three times with a 10% KHSO$_4$ solution (10 mL), once with a saturated NaHCO$_3$ solution and once with brine. The organic solution was dried over MgSO$_4$, filtered and concentrated in vacuo. Column chromatography (EtOAc:hexane::95:5) afforded three products after removal of solvent in vacuo: (1) 1,5-di-(t-butyloxycarbonyl)-2-methylindole, an oil (89 mg, 6% yield, R$_f$=0.8): $^1$H NMR (CDCl$_3$, 300 MHz): 8.10 (d, 1H, J=8), 8.09 (s, 1H), 7.87 (d, 1H, J=8), 6.37 (s, 1H), 2.60 (s, 3H), 1.69 (s, 9H), 1.62 (s, 9H); (2) the title product, a light orange solid (726 mg, 56% yield, Rf=0.5): $^1$H NMR (CDCl$_3$, 300 MHz): 10.0 (s, 1H0, 8.24 (d, 1H, J=8), 7.97 (d, 1H, J=2), 7.77 (dd, 1H, J=8, 2), 6.44 (s, 1H), 2.62 (d, 3H, J=1), 1.70 (s, 9H); (3) 5-formyl-2-methylindole, a light orange solid (139 mg, 17% yield, Rf=0.3): $^1$H NMR (CDCl$_3$, 300 MHz): 10.0 (s, 1H), 8.20 (br s, 1H), 7.71 (d, 1H, J=1), 7.68 (d, 1H, J=8), 7.37 (d, 1H, J=8), 6.37 (t, 1H, J=1), 2.48 (d, 3H, J=1); MS (ES+): 160 (C$_{10}$H$_{10}$NO, M++H).

Intermediate 5

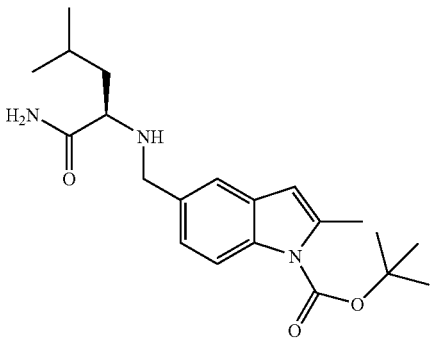

2R-(1-t-Butyloxycarbonyl-2-methylindol-5-ylmethylamino)-4-methyl-pentanamide. Following the procedure reported above for intermediate 2,5-formyl-2-methyl-1-t-butyloxycarbonylindole (259 mg, 1.0 mmol), D-leucinamide (130 mg, 1.0 mmol), sodium triacetoxyborohydride (636 mg, 3.0 mmol) and HOAc (0.34 mL, 6.0 mmol) were reacted in DCE (4 mL) to give the title product, a white solid (363 mg, 97% yield): $^1$H NMR (CDCl$_3$, 300 MHz): 8.04 (d, 1H, J=8), 7.34 (br s, 1H), 7.14 (dd, 2H, J=8,1), 6.28 (s, 1H), 5.35 (br s, 2H), 3.88 (d, 1H, J=12), 3.72 (d, 1H, J=12), 3.25–3.15 (m, 1H), 2.59 (s, 3H), 1.7–1.55 (m, 3H), 1.68 (s, 9H), 0.93(d, 3H, J=7), 0.84 (d, 3H, J=7); MS (ES+): 374 (C$_{21}$H$_{32}$N$_3$O$_3$, M$^+$+H).

Intermediate 6

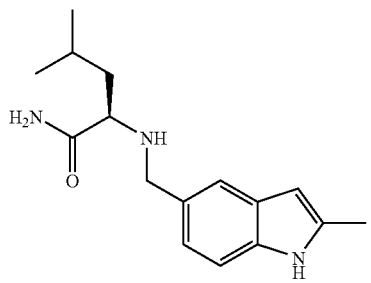

2R-(2-methylindol-5-ylmethylamino)-4-methyl-pentanamide. Following the procedure reported above for intermediate 2,5-formyl-2-methylindole (139 mg, 0.87 mmol), D-leucinamide (114 mg, 0.87 mmol), sodium triacetoxyborohydride (553 mg, 2.61 mmol) and HOAc (0.15 mL, 2.61 mmol) were reacted in DCE (4 mL) to give the title product, a white solid (212 mg, 89% yield): $^1$H NMR (CDCl$_3$, 300 MHz): 8.06 (br s, 1H), 7.40 (s, 1H), 7.23 (d, 1H, J=8), 7.01 (d, 1H, J=8), 6.17 (s, 1H), 5.65 (br s, 1H), 3.88 (d, 1H, J=12), 3.71 (d, 1H, J=12), 3.24–3.17 (m, 1H), 2.43 (s, 3H), 1.80–1.40 (m, 5H), 0.92(d, 3H, J=7), 0.82 (d, 3H, J=7); MS (ES+): 274 (C$_{16}$H$_{24}$N$_3$O, M++H).

Intermediates 7 and 8

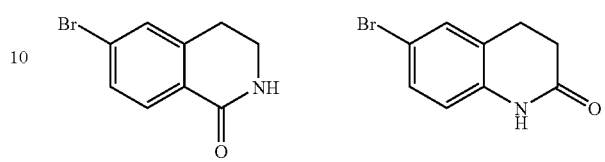

6-Bromo-1H-1,2,3,4-tetrahydroisoquinol-2-one and 6-bromo-2H-1,2,3,4-tetrahydroquinolone. 5-Bromoindan-1-one (44 g, 209 mmol) was dissolved in CHCl$_3$ (750 mL) with vigorous stirring and cooled to 0° C. Methanesulfonic acid (135 mL, 2090 mmol) was added dropwise. Sodium azide (40.7 g, 625 mmol) was added in portions over 30 min such that the internal temperature did not exceed 10° C. The reaction mixture was heated to reflux temperature and stirred for 2 h. The reaction mixture was cooled to room temperature and poured onto ice (1 kg) with manual stirring. The mixture was neutralized with NH$_4$OH. The layers were separated. The organic solution was dried over MgSO$_4$, filtered and concentrated in vacuo. Column chromatography (EtOAc) provided, after removal of solvent in vacuo: (1) 6-bromo-2H-1,2,3,4-quinol-1-one (10.7 g, 25% yield): $^1$H NMR (CDCl$_3$, 300 MHz): 8.11 (br s, 1H), 7.32 (d, 1H, J=1), 7.29 (dd, 1H, J=8, 1), 6.23 (br s, 1H), 6.25 (br s, 1H), 2.98 (t, 2H, J=7), 2.65 (t, 2H, J=7); MS (APCI+): 267, 269 (C$_{11}$H$_{12}$BrN$_2$O, M++H+CH$_3$CN) and (2) 6-bromo-1H-1,2,3,4-tetrahydroisoquinolone (21.5 g, 46% yield): $^1$H NMR (CDCl$_3$, 300 MHz): 7.95 (d, 1H, J=8), 7.51 (dd, 1H, J=8, 1), 7.21 (t, 1H, J=1), 6.25 (br s, 1H), 3.59 (t, 2H, J=7), 3.01 (t, 2H, J=7); MS (APCI+): 267, 269 (C$_{11}$H$_{12}$BrN$_2$O, M++H+CH$_3$CN).

Intermediate 9

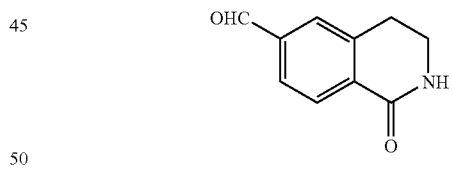

6-Formyl-1-oxo-1,2,3,4-tetrahydroquinoline. 6-Bromo-1H-1,2,3,4-tetrahydroisoquinol-1-one (420 mg, 1.9 mmol) and DMF (150 μL, 1.30 mmol) were dissolved in dry THF (8 mL) and the resulting solution was cooled to −78° C. with stirring. A solution of t-butyllithium (1.7 M in heptane, 3.3 mL, 5.58 mmol) was added dropwise over 5 min. The reaction mixture was stirred for 2 h at −78° C. HOAc (0.5 mL) was added and the reaction mixture was warmed gradually to room temperature. The mixture was diluted with EtOAc (25 mL). The organic solution was washed twice with a saturated NaHCO$_3$ (10 mL) and brine (5 mL). The organic layer was dried over MgSO$_4$, filtered and concentrated in vacuo to afford a pale yellow oil. Column chromatography (EtOAC:hexane::1:1) afforded, after removal of solvent in vacuo, a solid (107 mg, 33% yield): $^1$H NMR (DMSO-d6, 300 MHz): 10.04 (s, 1H), 8.20 (s, 1H), 8.01 (d, 1H, J=8), 7.85 (d, 1H, J=8), 7.86 (s, 1H), 3.40 (m, 2H), 3.01 (t, 2H, J=7); MS (APCI+): 217 ($C_{11}H_{13}N_2O_2$, M++H+$CH_3CN$).

Intermediate 10

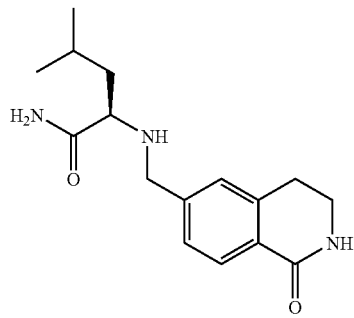

2R-(N-(1-oxo-1,2,3,4-tetrahydroisoquinolin-6-ylmethylamino)-4-methyl-pentanamide. Following the procedure reported above for intermediate 2,6-formyl-1-oxo-1,2,3,4-tetrahydroisoquinoline (Example 2, 100 mg, 0.57 mmol), D-leucinamide (74 mg, 0.57 mmol), sodium triacetoxyborohydride (362 mg, 1.71 mmol) and HOAc (0.2 mL, 3.42 mmol) were reacted in DCE (2 mL) to give the title product, a white solid (212 mg, 89% yield): $^1$H NMR (DMSO-d6, 300 MHz): 7.86 (br s, 1H), 7.76 (d, 1H, J=7), 7.40 (br s, 1H), 7.28 (d, 1H, J=7) 7.23 (br s, 1H), 7.0 (br s, 1H), 3.72 (d, 1H, J=12), 3.55 (d, 1H, J=12), 3.42–3.35 (m, 2H), 1.90–1.80 (m, 4H), 1.81–1.76 (m, 1H), 1.35–1.27 (m, 2H), 0.92(d, 3H, J=7), 0.82 (d, 3H, J=7); MS (ES+): 290 ($C_{16}H_{24}N_3O_2$, M++H).

Intermediate 11

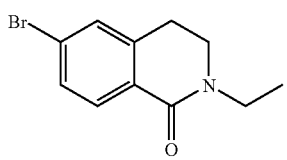

5-Bromo-2-ethyl-2H-1,2,3,4-tetrahydroisoquinol-1-one. 6-Bromo-1H-1,2,3,4-tetrahydroisoquinol-1-one (410 mg, 1.8 mmol) was dissolved in dry DMF (5 mL) and the resulting solution was cooled to −10° C. with stirring. A solution of sodium bis-trimethylsilylamide (1.0 M in THF, 2.0 mL, 2.0 mmol) was added dropwise over 10 min. Iodoethane (0.22 mL, 2.72 mmol) was added. The reaction mixture was warmed to room temperature over 2 h. The reaction mixture was diluted with EtOAc (50 mL). The organic solution was washed with water (5 ml), a 5% LiCl solution (2×5 mL) and brine (5 mL). The organic layer was dried over MgSO4, filtered and concentrated in vacuo to afford a pale yellow oil. Column chromatography (EtOAc: hexane::2:3) afforded, after removal of solvent in vacuo, a clear, colorless oil (330 mg, 72%): $^1$H NMR (CDCl$_3$, 300 MHz): 7.94 (d, 1H, J=8), 7.45 (dd, H, J=8, 2), 7.34 (d, H, J=2), 3.62 (q, 2H, J=7), 3.57 (t, 2H, J=7), 2.99 (t, 2H, J=7), 1.22 (t, 3H, J=7); MS (ES+): 254, 256 ($C_{11}H_{13}BrNO$, M++H); HRMS (ES+): Calcd for $C_{11}H_{13}BrNO$ (M++H): 254.0181; Found: 254.0172.

Intermediate 12

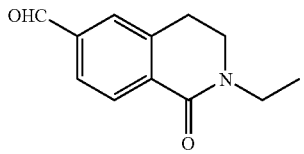

2-Ethyl-5-formyl-2H-1,2,3,4-tetrahydroisoquinolone. 6-Bromo-2-ethyl-1H-1,2,3,4-tetrahydroisoquinol-1-one (330 mg, 1.3 mmol) and DMF (102 μL, 1.30 mmol) were dissolved in dry THF (5 mL) and the resulting solution was cooled to −78° C. with stirring. A solution of t-butyllithium (1.7 M in heptane, 1.9 mL, 3.25 mmol) was added dropwise over 5 min. The reaction mixture was stirred for 2 h at −78° C. HOAc (0.5 mL) was added and the reaction mixture was warmed gradually to room temperature. The mixture was diluted with EtOAc (25 mL). The organic solution was washed twice with a saturated NaHCO$_3$ (10 mL) and brine (5 mL). The organic layer was dried over MgSO$_4$, filtered and concentrated in vacuo to afford a pale yellow oil. Column chromatography (EtOAC:hexane::1:1) afforded, after removal of solvent in vacuo, a solid (148 mg, 56% yield): $^1$H NMR (CDCl$_3$, 300 MHz): 10.06 (s, 1H), 8.25 (d, 1H, J=8), 7.83 (dd, 1H, J=8, 2), 7.72 (s, 1H), 3.80–3.58 (m, 4H), 3.09 (t, 2H, J=7), 1.25 (t, 3H, J=7); MS (APCI+): 203 ($C_{12}H_{13}NO_2$, M++H).

Intermediate 13

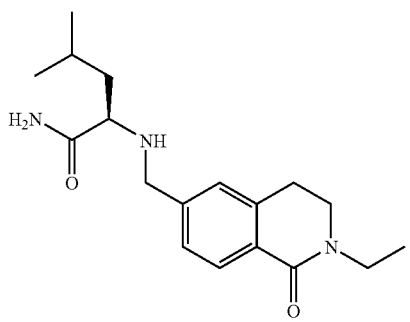

2R-(N-(1-oxo-2-ethyl-1,2,3,4-tetrahydroisoquinolin-6-ylmethylamino)-4-methyl-pentanamide. Following the procedure reported above for intermediate 2,2ethyl-5-formyl-2H-1,2,3,4-tetrahydroisoquinolone (145 mg, 0.7 mmol), D-leucinamide (93 mg, 0.7 mmol), sodium triacetoxyborohydride (451 mg, 2.1 mmol) and HOAc (0.24 mL, 4.3 mmol) were reacted in DCE (5 mL) to give the title product, a colorless oil (61 mg, 26% yield, purified by column chromatography using EtOAc): $^1$H NMR (CDCl$_3$, 300 MHz): 8.04 (d, 1H, J=8), 7.28–7.25 (m, 1H), 7.1 (s, 1H), 7.00 (s, 1H), 5.60 (s, 1H), 3.84 (d, 1H, J=14), 3.67 (d, 1H, J=14), 3.62 (t, 2H, J=7), 3.57 (q, 2H, J=7), 3.19–3.14 (m, 1H), 2.98 (t, 2H, J=7), 1.80–1.40 (m, 4H), 1.22 (t, 3H, J=7), 0.94 (d, 3H, J=7), 0.85 (d, 3H, J=7); MS (ES+): 318 ($C_{18}H_{28}N_3O_2$, M++H).

Intermediate 14

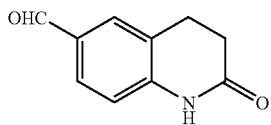

5-Formyl-1,2,3,4-tetrahydroquinol-2-one. Following the procedure reported above for 2-ethyl-5-formyl-2H-1,2,3,4-tetrahydroisoquinolone described above, 6-bromo-1,2,3,4-tetrahydroquinol-2-one (1.07 g, 4.73 mmol), a solution of t-butyllithium in heptane (1.7M, 9.7 mL, 16.6 mmol), DMF (0.37 mL, 4.73 mmol) and THF 35 mL) were combined. The reaction mixture was stirred at −78° C. for 4 h and HOAc (1 mL) was added. The previously described workup provided crude product. Column chromatography (EtOAc:hexane::1:1, then DCM:MeOH::97:3) and removal of solvent in vacuo provided a white solid (116 mg, 14% yield): $^1$H NMR: 9.90 (s, 1H), 8.0 (s, 1H), 7.77–7.74 (m, 2H), 6.89 (d, 1H, J=8), 3.07 (t, 2H, J=7), 2.71 (t, 2H, J=7).

Intermediate 15

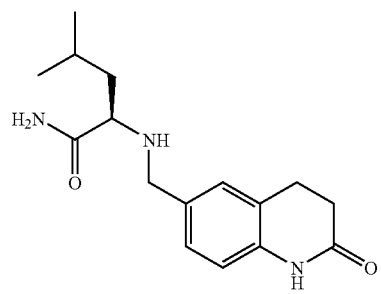

2R-(N-(2-oxo-1,2,3,4-tetrahydroquinolin-6-ylmethylamino)-4-methyl-pentanamide. Following the procedure reported above for 2R-(1-t-butyloxycarbonylindol-5-ylmethylamino)-4-methyl-pentanamide, 6-formyl-2H-1,2,3,4-tetrahydroquinolone (140 mg, 0.8 mmol), D-leucinamide (104 mg, 0.8 mmol), sodium triacetoxyborohydride (509 mg, 2.4 mmol) and HOAc (0.27 mL, 4.8 mmol) were reacted in DCE (3 mL) to give the title product, a white solid (61 mg, 26% yield, recrystallized from EtOAc): $^1$H NMR (DMSO-d6, 300 MHz): 10.0 (s, 1H), 7.37 (s, 1H), 7.08 (s, 1H), 7.04 (d, 1H, J=8), 6.98 (s, 1H), 6.75 (d, 1H, J=8), 3.58 (d, 1H, J=13), 3.35 (d, 1H, J=13), 2.90 (t, 1H, J=7), 2.83 (t, 2H, J=7), 2.43 (t, 2H, J=7), 1.76–1.70 (m, 1H), 1.25–1.17 (m, 2H), 0.84 (d, 3H, J=7), 0.76 (d, 3H, J=7); MS (ES+): 290 ($C_{16}H_{24}N_3O_2$, M++H).

Intermediate 16

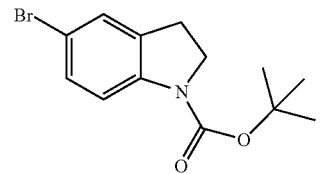

5-Bromo-1-t-butyloxycarbonylindoline. 5-Bromoindoline (3.96 g, 20 mmol), di-t-butylcarbonate (4.37 g, 20 mmol), 4-dimethylaminopyridine (2.69 g, 22 mmol) and CH3CN (50 mL) were mixed and stirred at room temperature for 16 h. The reaction mixture was diluted with EtOAc (300 mL) and the organic solution was washed successively with water (50 mL), a 1 N HCl solution (50 mL), a saturated NaHCO$_3$ solution (2×50 mL) and brine (25 mL). The organic layer was dried over MgSO$_4$, filtered and concentrated in vacuo to afford a solid. Trituration with hexane and drying in vacuo provided a white solid (2.26 g, 38% yield): $^1$H NMR (DMSO-d6, 300 MHz): 7.36 (s, 1H), 7.29 (d, 2H, J=7), 3.86 (t, 2H, J=7), 3.04 (t, 2H, J=7), 1.48 (s, 9H).

Intermediate 17

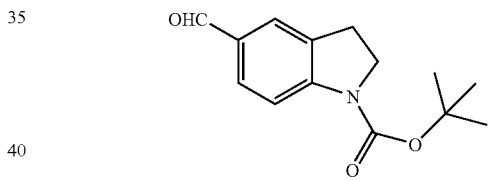

1-t-Butyloxycarbonyl-5-formylindoline. 5-Bromo-1-t-butyloxycarbonylindoline (2.0 g, 6.7 mmol) and DMF (0.53 mL, 6.7 mmol), were dissolved in THF (30 mL) and the resulting solution was cooled to −78° C. with stirring under a nitrogen atmosphere. A solution of t-butyllithium in pentane (1.7 M, 10.3 mL, 17.5 mmol) was added dropwise over 5 min. The reaction mixture was stirred for 2 h; then HOAc (3 mL) was added. The cloudy mixture was warmed to ambient temperature over 30 min and diluted with EtOAc (100 mL). Successive washings with a saturated Na$_2$CO$_3$ solution (2×10 mL) and then brine (10 mL) were performed. Drying over Na$_2$SO$_4$, filtration and removal of solvent in vacuo gave an oil. Column chromatography (EtOAc:hexane: 1:9, then 1:1) and removal of solvent in vacuo provided two products, both were white solids: (1) 1-t-butyloxycarbonylindoline (270 mg, 18% yield): $^1$H NMR (CDCl$_3$, 300 MHz): 7.18–7.10 (m, 2H), 6.92 (t, 1H, J=7), 3.97 (t, 2H, J=7), 3.08 (t, 3H, J=7), 1.57 (s, 9H); MS (APCI+): 220 ($C_{13}H_{18}NO_2$, M++H) and (2) the title product (650 mg, 39% yield): $^1$H NMR (CDCl$_3$, 300 MHz): 9.86 (s, 1H), 7.9 (br s, 1H), 7.70–7.65 (m, 2H), 4.06 (t, 2H, J=7), 3.15 (t, 2H, J=7), 1.58 (s, 9H); MS (ES+): 248 ($C_{14}H_{18}NO_3$, M++H).

Intermediates 18 through 27

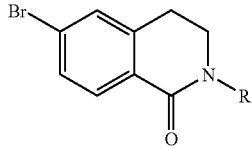

(18) R = Me
(19) R = Pr
(20) R = Bu
(21) R = CH₂Ph
(22) R = CH₂CH₂OMe
(23) R = CH₂-cyclopropyl
(24) R = CH₂-cyclobutyl
(25) R = CH₂-(2-pyridyl)
(26) R = 2-propyl
(27) R = 3-pentyl Following the procedure described for intermediate 11 (5-bromo-2-ethyl-2H-1,2,3,4-tetrahydroisoquinol-1-one, the following compounds were prepared from the appropriate halide compound:

Intermediate 18

5-Bromo-2-methyl-2H-1,2,3,4-tetrahydroisoquinol-1-one. 404 mg (84% yield from CH₃I); $^1$H NMR (DMSO-d6, 300 MHz): 7.76 (d, 1H, J=8), 7.54 (s, 1H), 7.53 (d, 1H, J=8), 3.53 (t, 2H, J=7), 3.00 (s, 3H), 2.97 (t, 2H, J=7).

Intermediate 19

5-Bromo-2-propyl-2H-1,2,3,4-tetrahydroisoquinol-1-one. 354 mg (66% yield from C₃H₇I); $^1$H NMR (CDCl₃, 300 MHz): 7.93 (d, 1H, J=8), 7.47 (dd, 1H, J=8,2), 7.34 (d, 1H, J=2), 3.56–3.52 (m, 4H), 2.96 (t, 2H, J=7), 1.66–1.56 (m, 2H), 1.44–1.34 (m, 2H), 0.96 (t, 3H, J=7); MS (APCI+): 323, 325 (C₁₃H₁₇BrN₂O, M++H+CH₃CN).

Intermediate 20

5-Bromo-2-butyl-2H-1,2,3,4-tetrahydroisoquinol-1-one. 431 mg (76% yield from C₄H₉I); $^1$H NMR (CDCl₃, 300 MHz): 7.93 (d, 1H, J=8), 7.46 (dd, 1H, J=8,2), 7.34 (d, 1H, J=2), 3.56–3.52 (m, 4H), 2.96 (t, 2H, J=7), 1.72–1.56 (m, 2H), 0.96 (t, 3H, J=7); MS (APCI+): 309, 311 (C₁₂H₁₅BrN₂O, M++H+CH₃CN).

Intermediate 21

5-Bromo-2-benzyl-2H-1,2,3,4-tetrahydroisoquinol-1-one. 528 mg (84% yield from C₆H₅CH₂Br); $^1$H NMR (CDCl₃, 300 MHz): 8.00 (d, 1H, J=8), 7.49 (dd, 1H, J=8,2), 7.37–7.30 (m, 5H), 4.78 (s, 2H), 3.49 (t, 2H, J=7), 2.91 (t, 3H, J=7); MS (ES+): 316, 318 (C₁₆H₁₅BrNO, M++H).

Intermediate 22

5-Bromo-2-(2-methoxyethyl)-2H-1,2,3,4-tetrahydroisoquinol-1-one. 434 mg (76% yield from CH₃OCH₂CH₂Br); $^1$H NMR (CDCl₃, 300 MHz): 7.93 (d, 1H, J=8), 7.47 (dd, 1H, J=8,2), 7.34 (d, 1H, J=2), 3.76–3.6 (m, 6H), 3.36 (s, 3H), 2.96 (t, 2H, J=7); MS (APCI+): 285, 287 (C₁₂H₁₅BrNO₂, M++H).

Intermediate 23

5-Bromo-2-cyclopropylmethyl-2H-1,2,3,4-tetrahydroisoquinol-1-one. 379 mg (68% yield from C₃H₅CH₂Br); $^1$H NMR (CDCl₃, 300 MHz): 7.95 (d, 1H, J=8), 7.47 (dd, 1H, J=8, 2), 7.34 (d, 1H, J=2), 3.65 (t, 2H, J=7), 3.46 (d, 2H, J=7), 2.99 (t, 2H, J=7), 1.11–1.01 (m, 1H), 0.57–0.51 (m, 2H), 0.33–0.27 (m, 2H); MS (APCI+): 281, 283 (C₁₃H₁₅BrNO, M++H).

Intermediate 24

5-Bromo-2-cyclobutylmethyl-2H-1,2,3,4-tetrahydroisoquinol-1-one. 364 mg (62% yield from C₄H₇CH₂Br); $^1$H NMR (CDCl₃, 300 MHz): 7.94 (d, 1H, J=8), 7.46 (dd, 1H, J=8, 2), 7.34 (d, 1H, J=2), 3.59 (d, 2H, J=7), 3.52 (t, 2H, J=7), 2.93 (t, 2H, J=7), 2.67 (quintet, 1H, J=7), 2.09–2.01 (m, 2H), 1.94–1.76 (m, 4H); MS (APCI+): 294, 296 (C₁₄H₁₇BrNO, M++H).

Intermediate 25

5-Bromo-2-(pyrid-2-ylmethyl)-2H-1,2,3,4-tetrahydroisoquinol-1-one. 210 mg (33% yield from picolyl bromide hydrobromide and 3.0 equivalents NaHMDS); MS (APCI+): 317, 319 (C₁₅H₁₄BrN₂O, M++H).

Intermediate 26

5-Bromo-2-(2-propyl)-2H-1,2,3,4-tetrahydroisoquinol-1-one. 432 mg (33% yield from 2-iodopropane and 2.2 equivalents NaH); $^1$H NMR (CDCl₃, 300 MHz): 7.93 (d, 1H, J=8), 7.45 (dd, 1H, J=8, 1), 7.32 (d, 1H, J=1), 5.05 (septet, 1H, J=7), 3.41 (t, 2H, J=7), 2.90 (t, 2H, J=7), 1.18 (d, 6H, J=7); MS (APCI+): 268, 270 (C₁₄H₁₄BrNO, M+).

Intermediate 27

5-Bromo-2-(3-pentyl)-2H-1,2,3,4-tetrahydroisoquinol-1-one. 1.17 g (45% yield from 3-bromopentane and 1.1 equivalents LiHMDS); MS (APCI+): 296, 298 (C₁₄H₁₆BrNO, M+).

Intermediates 28 through 37

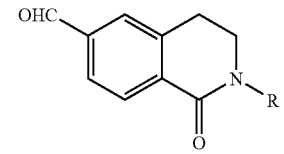

(28) R = Me
(29) R = Pr
(30) R = Bu
(31) R = CH₂Ph
(32) R = CH₂CH₂OMe
(33) R = CH₂-cyclopropyl
(34) R = CH₂-cyclobutyl
(35) R = CH₂-(2-pyridyl)
(36) R = 2-propyl
(37) R = 3-pentyl Following the general procedure described in intermediate 12, the following compounds were prepared using the appropriate 5-bromo-2H-1,2,3,4-tetrahydroisoquinol-1-one:

Intermediate 28

5-Formyl-2-methyl-2H-1,2,3,4-tetrahydroisoquinol-1-one. 80 mg (pale yellow oil, 32% yield); $^1$H NMR (CDCl$_3$, 300 MHz): 10.1 (s, 1H), 8.25 (d, 1H, J=7), 7.83 (dd, 1H, J=8, 2), 7.72 (d, 1H, J=2), 3.62 (t, 2H, J=7), 3.19 (s, 3H), 3.10 (t, 2H, J=7).

Intermediate 29

5-Formyl-2-propyl-2H-1,2,3,4-tetrahydroisoquinol-1-one. 89 mg (white solid, 32% yield); $^1$H NMR (CDCl$_3$, 300 MHz): 10.1 (s, 1H), 8.25 (d, 1H, J=7), 7.83 (dd, 1H, J=8, 2), 7.72 (d, 1H, J=2), 3.66–3.54 (m, 4H), 3.08 (t, 2H, J=7), 1.72–1.56 (sextet, 2H, J=7), 0.98 (t, 3H, J=7); MS (ES+): 218 (C$_{13}$H$_{16}$NO$_2$, M++H).

Intermediate 30

5-Formyl-2-butyl-2H-1,2,3,4-tetrahydroisoquinol-1-one. 123 mg (pale yellow oil, 36% yield); $^1$H NMR (CDCl$_3$, 300 MHz): 10.1 (s, 1H), 8.25 (d, 1H, J=7), 7.83 (dd, 1H, J=8, 2), 7.72 (d, 1H, J=2), 3.66–3.57 (m, 4H), 3.08 (t, 2H, J=7), 1.64 (quintet, 2H, J=7), 1.39 (sextet, 2H, J=7), 0.97 (t, 3H, J=7); MS (ES+): 232 (C$_{14}$H$_{18}$NO$_2$, M++H).

Intermediate 31

5-Formyl-2-benzyl-2H-1,2,3,4-tetrahydroisoquinol-1-one. 90 mg (pale yellow oil, 21% yield); $^1$H NMR (CDCl$_3$, 300 MHz): 10.1 (s, 1H), 8.32 (d, 1H, J=7), 7.87 (dd, 1H, J=8, 2), 7.71 (d, 1H, J=2), 7.36–7.26 (m, 5H), 4.80 (s, 2H), 3.54 (t, 2H, J=7), 3.03 (t, 2H, J=7); MS (ES+): 266 (C$_{17}$H$_{16}$NO$_2$, M++H).

Intermediate 32

5-Formyl-2-(2-methoxyethyl)-2H-1,2,3,4-tetrahydroisoquinol-1-one. 49 mg (pale yellow oil, 14% yield); $^1$H NMR (CDCl$_3$, 300 MHz): 10.1 (s, 1H), 8.23 (d, 1H, J=7), 7.83 (dd, 1H, J=8, 2), 7.72 (d, 1H, J=2), 3.79–3.63 (m, 6H), 3.36 (s, 3H), 3.07 (t, 2H, J=7); MS (ES+): 234 (C$_{13}$H$_{16}$NO$_3$, M++H).

Intermediate 33

5-Formyl-2-cyclopropylmethyl-2H-1,2,3,4-tetrahydroisoquinol-1-one. 49 mg (pale yellow oil, 16% yield); $^1$H NMR (CDCl$_3$, 300 MHz): 10.1 (s, 1H), 8.26 (d, 1H, J=7), 7.83 (dd, 1H, J=8, 2), 7.72 (d, 1H, J=2), 3.70 (t, 2H, J=7), 3.50 (d, 2H, J=7), 3.10 (t, 2H, J=7), 1.11–1.05 (m, 1H), 0.59–0.53 (m, 2H), 0.35–0.30 (m, 2H); MS (ES+): 230 (C$_{14}$H$_{16}$NO$_2$, M++H).

Intermediate 34

5-Formyl-2-cyclobutylmethyl-2H-1,2,3,4-tetrahydroisoquinol-1-one. 90 mg (white solid, 31% yield); $^1$H NMR (CDCl$_3$, 300 MHz): 10.1 (s, 1H), 8.25 (d, 1H, J=7), 7.83 (dd, 1H, J=8, 2), 7.71 (d, 1H, J=2), 3.63 (d, 2H, J=7), 3.57 (t, 2H, J=7), 3.05 (t, 2H, J=7), 2.70 (quintet, 1H, J=7), 2.10–2.03 (m, 2H), 1.98–1.77 (m, 4H); MS (ES+): 244 (C$_{15}$H$_{18}$NO$_2$, M++H).

Intermediate 35

5-Formyl-2-(pyrid-2-ylmethyl)-2H-1,2,3,4-tetrahydroisoquinol-1-one. 42 mg (pale yellow oil, 17% yield); $^1$H NMR (CDCl$_3$, 300 MHz): 10.1 (s, 1H), 8.56 (dd, 1H, J=2,1), 8.29 (d, 1H, J=7), 7.85 (dd, 1H, J=8, 2), 7.72–7.65 (m, 2H), 7.40 (d, 1H, J=7), 7.23–7.20 (m, 1H), 4.93 (s, 2H), 3.73 (t, 2H, J=7), 3.08 (t, 2H, J=7); MS (ES+): 267 (C$_{16}$H$_{15}$N$_2$O$_2$, M++H).

Intermediate 36

5-Formyl-2-(2-propyl)-2H-1,2,3,4-tetrahydroisoquinol-1-one. 673 mg (pale yellow oil, 65% yield); $^1$H NMR (CDCl$_3$, 300 MHz): 10.0 (s, 1H), 8.24 (d, 1H, J=7), 7.83 (d, 1H, J=7), 7.70 (s, 1H), 5.08 (septet, 1H, J=7), 3.47 (t, 2H, J=7), 3.02 (t, 2H, J=7), 1.21 (d, 6H, J=7); MS (ES+): 218 (C$_{13}$H$_{14}$NO$_2$, M++H).

Intermediate 37

5-Formyl-2-(3-pentyl)-2H-1,2,3,4-tetrahydroisoquinol-1-one. 673 mg (pale yellow oil, 65% yield); $^1$H NMR (CDCl$_3$, 300 MHz): 10.1 (s, 1H), 8.26 (d, 1H, J=7), 7.82 (d, 1H, J=7), 7.72 (s, 1H), 4.66 (septet, 1H, J=7), 3.38 (t, 2H, J=7), 3.03 (t, 2H, J=7), 1.62–1.47 (m, 4H), 0.91 (t, 6H, J=7); MS (ES+): 246 (C$_{15}$H$_{20}$NO$_2$, M++H).

Intermediates 38 through 45

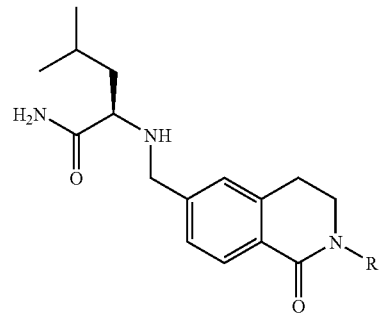

(38) R = Me
(39) R = Pr
(40) R = Bu
(41) R = CH$_2$Ph
(42) R = CH$_2$CH$_2$OMe
(43) R = CH$_2$-cyclopropyl
(44) R = CH$_2$-cyclobutyl
(45) R = CH$_2$-(2-pyridyl)

Following the procedures described in intermediate 2, the following compounds were prepared from the appropriate 5-formyl-2H-1,2,3,4-tetrahydroquinol-1-one:

Intermediate 38

2R-(1-methyl-2-oxo-1,2,3,4-tetrahydroisoquinolin-6-yl-methylamino)-4-methyl-pentanamide. 44 mg (pale yellow oil, 95% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.87 (br s, 1H), 3.84 (d, 1H, J=14), 3.73 (s, 3H), 3.67 (d, 1H, J=14), 3.58 (t, 1H, J=7), 3.22–3.16 (m, 1H), 3.15 (s, 3H), 3.14 (t, 2H, J=7), 1.95 (br s, 1H), 1.80–1.60 (m, 3H), 0.93 (d, 3H, J=7), 0.84 (d, 3H, J=7); MS (ES+): 607 (C$_{34}$H$_{50}$N$_6$O$_4$, 2M++2H).

Intermediate 39

2R-(1-propyl-2-oxo-1,2,3,4-tetrahydroisoquinolin-6-yl-methylamino)-4-methyl-pentanamide. 42 mg (pale yellow oil, 93% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.87 (br s, 1H), 3.84 (d, 1H, J=14), 3.73 (s, 3H), 3.67 (d, 1H, J=14), 3.58 (t, 2H, J=7), 3.22–3.16 (m, 1H), 3.15 (s, 3H), 3.14 (t, 2H, J=7), 1.95 (br s, 1H), 1.80–1.60 (m, 3H), 0.93 (d, 3H, J=7), 0.84 (d, 3H, J=7); MS (ES+): 664 (C$_{38}$H$_{56}$N$_6$O$_4$, 2M++2H).

Intermediate 40

2R-(1-butyl-2-oxo-1,2,3,4-tetrahydroisoquinolin-6-ylmethylamino)-4-methyl-pentanamide. 33 mg (pale yellow oil, 90% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.87 (br s, 1H), 3.84 (d, 1H, J=14), 3.67 (d, 1H, J=14), 3.60–3.50 (m, 4H), 3.19–3.14 (m, 1H), 2.97 (t, 2H, J=7), 2.15 (br s, 1H), 1.80–1.30 (m, 6H), 0.98 (t, 3H, J=7), 0.93 (d, 3H, J=7), 0.84 (d, 3H, J=7); MS (ES+): 692 (C$_{40}$H$_{64}$N$_6$O$_4$, 2M++2H).

Intermediate 41

2R-(1-benzyl-2-oxo-1,2,3,4-tetrahydroisoquinolin-6-yl-methylamino)-4-methyl-pentanamide. 37 mg (pale yellow oil, 99% yield); $^1$H NMR (CDCl$_3$, 300 MHz): 8.03 (d, 1H, J=8), 7.38–7.25 (m, 6H), 7.11 (s, 1H), 7.02 (br s, 1H), 5.87 (br s, 1H), 4.79 (s, 2H), 3.84 (d, 1H, J=14), 3.67 (d, 1H, J=14), 3.48 (t, 2H, J=7), 3.19–3.14 (m, 1H), 2.92 (t, 2H, J=7), 2.15 (br s, 1H), 1.75–1.45 (m, 3H), 0.93 (d, 3H, J=7), 0.84 (d, 3H, J=7); MS (ES+): 760 (C$_{46}$H$_{60}$N$_6$O$_4$, 2M++2H).

Intermediate 42

2R-(1-(2-methoxyethyl)-2-oxo-1,2,3,4-tetrahydroisoquinolin-6-ylmethylamino)-4-methyl-pentanamide. 34 mg (pale yellow oil, 90% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.87 (br s, 1H), 3.84 (d, 1H, J=14), 3.76–3.60 (m, 7H), 3.36 (s, 3H), 3.16 (dd, 1H, J=5, 5), 2.97 (t, 2H, J=7), 1.95 (br s, 1H), 1.70–1.40 (m, 3H), 0.93 (d, 3H, J=7), 0.84 (d, 3H, J=7); MS (ES+): 696 (C$_{38}$H$_{60}$N$_6$O$_6$, 2M++2H).

Intermediate 43

2R-(1-cyclopropylmethyl-2-oxo-1,2,3,4-tetrahydroisoquinolin-6-ylmethylamino)-4-methyl-pentanamide. 33 mg (pale yellow oil, 90% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.80 (br s, 1H), 3.84 (d, 1H, J=14), 3.67 (d, 1H, J=14), 3.63 (t, 2H, J=7), 3.47 (d, 2H, J=7), 3.17 (dd, 1H, J=5, 5), 3.00 (t, 2H, J=7), 1.85 (br s, 1H), 1.70–1.40 (m, 3H), 1.15–1.00 (m, 1H), 0.93 (d, 3H, J=7), 0.84 (d, 3H, J=7), 0.60–0.55 (m, 2H), 0.35–0.25 (m, 2H); MS (ES+): 688 (C$_{40}$H$_{60}$N$_6$O$_4$, 2M++2H).

Intermediate 44

2R-(1-cyclobutylmethyl-2-oxo-1,2,3,4-tetrahydroisoquinolin-6-ylmethylamino)-4-methyl-pentanamide. 40 mg (pale yellow oil, 91% yield); $^1$H NMR (CDCl$_3$, 300 MHz): 8.03 (d, 1H, J=8), 7.27 (br d, 1H, J=8), 7.11 (s, 1H), 7.02 (br s, 1H), 5.85 (br s, 1H), 3.84 (d, 1H, J=14), 3.67 (d, 1H, J=14), 3.63 (d, 2H, J=7), 3.47 (t, 2H, J=7), 3.20–3.15 (m, 1H), 2.94 (t, 2H, J=7), 2.78–2.68 (m, 1H), 2.15–1.45 (m, 9H), 0.93 (d, 3H, J=7), 0.84 (d, 3H, J=7); MS (ES+): 716 (C$_{42}$H$_{62}$N$_6$O$_4$, 2M++2H).

Intermediate 45

2R-(1-(pyrid-2-ylmethyl-2-oxo-1, 2, 3, 4-tetrahydroisoquinolin-6-ylmethylamino)-4-methyl-pentanamide. 49 mg (pale yellow oil, 99% yield); $^1$H NMR (CDCl$_3$, 300 MHz): 8.55 (dd, 1H, J=2,1), 8.09 (d, 1H, J=8), 7.64 (td, 1H, J=8, 2), 7.38 (d, 1H, J=8), 7.30 (d, 1H, J=8), 7.27–7.18 (m, 1H), 7.12 (s, 1H), 6.96 (br s, 1H), 5.75 (br s, 1H), 4.91 (s, 2H), 3.84 (d, 1H, J=14), 3.70 (d, 1H, J=14), 3.65 (t, 2H, J=7), 3.20–3.13 (m, 1H), 2.99 (t, 2H, J=7), 1.97–1.40 (m, 4H), 0.93 (d, 3H, J=7), 0.85 (d, 3H, J=7); MS (APCI+): 381 (C$_{22}$H$_{29}$N$_4$O$_2$, M++H).

Intermediate 46

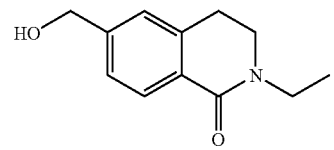

2-Ethyl-5-hydroxymethyl-2H-1,2,3,4-tetrahydroisoquinolone. 2-Ethyl-5-formyl-2H-1,2,3,4-tetrahydroisoquinolone (540 mg, 2.66 mmol) was dissolved in MeOH (10 mL) with stirring at room temperature. NaBH$_4$ (131 mg, 3.45 mmol) was added in one portion and stirring was continued for 3 h. The reaction was quenched with 0.1N HCl solution (1 mL). Three extractions with EtOAc (25 mL) were performed. The combined organic layers were washed twice with a saturated Na$_2$CO$_3$ solution (5 mL), dried over Na$_2$SO$_4$ and filtered. Removal of solvent in vacuo provided a colorless oil. Column chromatography (CH$_2$Cl$_2$:MeOH:: 95:5) and concentration of the fractions in vacuo gave a pale yellow oil (545 mg, 100% yield): $^1$H NMR (CDCl$_3$, 300 MHz): 7.98 (d, 1H, J=8), 7.25 (d, 1H, J=8), 7.19 (s, 1H), 4.71 (d, 2H, J=6), 3.61 (q, 2H, J=7), 3.54 (t, 2H, J=7), 2.96 (t, 2H, J=7), 2.54 (t, 1H, J=7), 1.21 (t, 3H, J=7); MS (APCI+): 205 (C$_{12}$H$_{16}$NO$_2$, M++H).

Intermediate 47

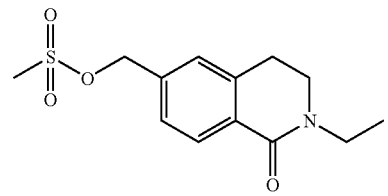

2-Ethyl-5-methanesulfonyloxymethyl-2H-1,2,3,4-tetrahydroisoquinolone. 2-Ethyl-5-hydroxymethyl-2H-1,2,3,4-tetrahydroisoquinolone (280 mg, 1.36 mmol) was dissolved in CH$_2$Cl$_2$ (5 mL) and the resulting solution was cooled to 0° C. with stirring. Et$_3$N (0.23 mL, 1.63 mmol) was added in one portion. Followed by methanesulfonyl chloride (0.12 mL, 1.50 mmol). Stirring was continued for 1 h. The reaction was quenched with ice water (1 mL). Three extractions with EtOAc (15 mL) were performed. The combined organic layers were washed twice with brine (5 mL), dried over Na$_2$SO$_4$ and filtered. Removal of solvent in vacuo provided a colorless oil as crude product which was carried on to subsequent reactions (350 mg): $^1$H NMR (CDCl$_3$, 300 MHz): 8.11 (d, 1H, J=8), 7.36 (dd, 1H, J=8,1), 7.24 (d, 1H, J=1), 5.24 (s, 2H), 3.68 (q, 2H, J=7), 3.58 (t, 2H, J=7), 3.00 (t, 2H, J=7), 2.98 (s, 3H), 1.21 (t, 3H, J=7); MS (APCI+): 284 (C$_{13}$H$_{18}$NO$_2$S, M++H).

Intermediates 48 and 49

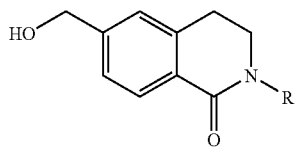

(48) R = 2-propyl
(49) R = 3-pentyl

Following the procedure described for intermediate 46, the following compounds were prepared:

Intermediate 48

2-(2-Propyl)-5-hydroxymethyl-2H-1,2,3,4-tetrahydroisoquinolone. 453 mg (65% yield): $^1$H NMR (CDCl$_3$, 300 MHz): 8.05 (d, 1H, J=7), 7.29 (d, 1H, J=7), 7.19 (s, 1H), 5.09 (septet, 1H, J=7), 4.72 (s, 2H), 3.42 (t, 2H, J=7), 2.93 (t, 2H, J=7), 1.7 (br s, 1H), 1.94 (d, 6H, J=7); MS (ES+): 220 (C$_{13}$H$_{18}$NO$_2$, M++H).

Intermediate 49

2-(3-Pentyl)-5-hydroxymethyl-2H-1,2,3,4-tetrahydroisoquinolone. 670 mg (90% yield): $^1$H NMR (CDCl$_3$, 300 MHz): 8.06 (d, 1H, J=7), 7.28 (d, 1H, J=7), 7.20 (s, 1H), 4.72 (s, 2H), 4.65 (quintet, 1H, J=7), 3.34 (t, 2H, J=7), 2.94 (t, 2H, J=7), 1.76 (br s, 1H), 1.57–1.44 (m, 4H), 0.90 (t, 6H, J=7); MS (ES+): 248 (C$_{15}$H$_{22}$NO$_2$, M++H).

Intermediates 50 and 51

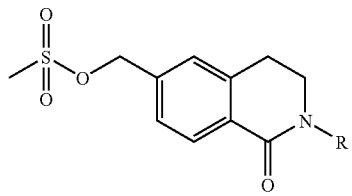

(50) R = 2-propyl
(51) R = 3-pentyl

Following the procedure described in intermediate 47, the following compounds were prepared:

Intermediate 50

2-(2-Propyl)-5-methanesulfonyloxymethyl-2H-1,2,3,4-tetrahydroisoquinolone. 614 mg (99% yield): $^1$H NMR (CDCl$_3$, 300 MHz): 8.11 (d, 1H, J=8), 7.35 (d, 1H, J=8), 7.23 (s, 1H), 5.24 (s, 2H), 5.07 (septet, 1H, J=7), 3.43 (t, 2H, J=7), 2.96 (t, 2H, J=7), 2.95 (s, 3H), 1.21 (d, 6H, J=7); MS (ES+): 298 (C$_{14}$H$_{20}$NO$_4$S, M++H).

Intermediate 51

2-(3-Pentyl)-5-methanesulfonyloxymethyl-2H-1,2,3,4-tetrahydroisoquinolone. 555 mg (63% yield): $^1$H NMR (CDCl$_3$, 300 MHz): 8.13 (d, 1H, J=8), 7.36 (d, 1H, J=8), 7.25 (s, 1H), 5.24 (s, 2H), 4.65 (quintet, 1H, J=7), 3.34 (t, 2H, J=7), 2.97 (t, 2H, J=7), 2.97 (s, 3H), 1.63–1.45(m, 4H), 0.90 (t, 6H, J=7); MS (ES+): 326 (C$_{16}$H$_{24}$NO$_4$S, M++H).

EXAMPLE 1

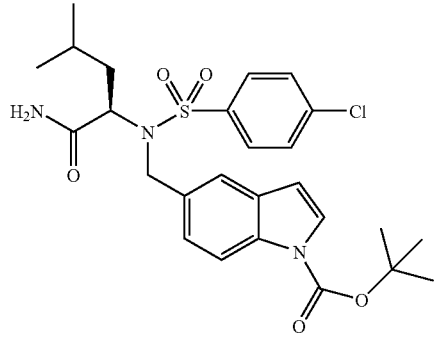

2R-(N-1-t-butyloxycarbonylindol-5-ylmethyl-N-4-chlorophenylsulfonylamino)-4-methyl-pentanamide. A mixture of 2R-(1-t-butyloxycarbonylindol-5-ylmethylamino)-4-methyl-pentanamide (360 mg, 1.0 mmol), 4-chlorophenylsulfonylchloride (253 mg, 1.2 mmol), Et$_3$N (0.21 mL, 1.5 mmol) and 4-dimethylaminopyridine (243 mg, 2.0 mmol) in DCM (2 mL) was stirred at room temperature for 16 h. The reaction mixture was diluted tenfold with EtOAc. The organic mixture was washed with a 1N HCl solution (10 mL), a saturated NaHCO$_3$ solution (10 mL) and brine (10 mL). Drying over MgSO$_4$, filtration and concentration in vacuo provided a solid. Column chromatography (EtOAc: hexane::3:7) and removal of solvent in vacuo provided a white solid (384 mg, 72% yield): $^1$H NMR (CDCl$_3$, 300 MHz): 8.07 (d, 1H, J=8), 7.70 (d, 2H, J=8), 7.67 (d, 1H, J=4), 7.61 (d, 1H, J=1), 7.45 (d, 2H, J=8), 7.26 (dd, 1H, J=8, 2), 6.53 (d, 1H, J=1), 6.28 (s, 1H), 5.15 (s, 1H), 4.68 (d, 1H, J=16), 4.48 (d, 1H, J=16), 4.33 (t, 1H, J=7), 1.92 (quintet, 1H, J=7), 1.69 (s, 9H), 1.40–1.28 (m, 2H), 0.76 (d, 3H, J=7), 0.69 (d, 3H, J=7); MS (ES+): 534 (C$_{26}$H$_{33}$ClN$_3$O$_5$S, M++H).

EXAMPLE 2

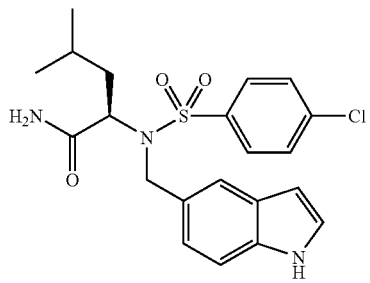

2R-(N-indol-5-ylmethyl-N-4-chlorophenylsulfonyl) amino-4-methyl-pentanamide. 2R-(N-1-t-butyloxycarbonylindol-5-ylmethyl-N-4-chlorophenylsulfonyl)amino-4-methyl-pentanamide (53 mg, 0.1 mmol), trifluoroacetic acid (0.25 mL) and DCM (1 mL) were mixed and the solution was stirred for 3 h at room temperature. The reaction mixture was diluted with EtOAc (10 mL) and the combined organic solution was washed with a saturated NaHCO$_3$ solution (10 mL), then brine (10 mL). The organic layer was dried over MgSO4, filtered and concentrated in vacuo to give a white solid (12 mg, 28% yield): optical purity>99% (HPLC: AD column, iPrOH:hexane: 1:4), HPLC log P=3.81 (pH=7.0); $^1$H NMR (CDCl$_3$, 300 MHz): 8.18 (s, 1H), 7.67 (dd, 2H, J=8,2), 7.58 (s, 1H), 7.40 (dd, 2H, J=8,2), 7.32 (d, 1H, J=8), 7.24–7.18 (m, 2H), 6.52–5.48 (m, 1H), 6.19 (s, 1H), 5.08 (s, 1H), 4.65 (d, 1H, J=15), 4.68 (d, 1H, J=15), 4.28 (t, 1H, J=7), 1.96–1.90 (m, 1H), 1.35–1.28 (m, 2H), 0.76 (d, 3H, J=7), 0.69 (d, 3H, J=7); HRMS (ES+): Calcd for C$_{21}$H$_{24}$ClN$_3$NaO$_3$S (M++Na): 456.1125, Found: 456.1111.

EXAMPLE 3

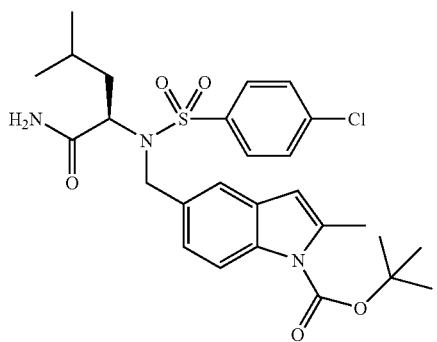

2R-(N-(1-t-Butyloxycarbonyl-2-methylindol-5-ylmethyl)-N-4-chlorophenylsulfonyl)amino-4-methyl-pentanamide. 2R-(1-t-Butyloxycarbonyl-2-methylindol-5-ylmethylamino)-4-methyl-pentanamide (360 mg, 0.96 mmol), 4-chlorophenylsulfonylchloride (224 mg, 1.06 mmol) and pyridine (2 mL) were stirred at ambient temperature for 16 h. The reaction mixture was diluted with EtOAc (20 mL), then washed with water (10 mL) and brine (10 mL). Drying over MgSO$_4$, filtration and concentration in vacuo provided a solid. Column chromatography (EtOAc:hexane::1:1, then EtOAc) and removal of solvent in vacuo gave the title product, an orange solid (72 mg, 14% yield): $^1$H NMR (CDCl$_3$, 300 MHz): 7.99 (d, 1H, J=9), 7.67 (dd, 2H, J=7, 2), 7.42 (dd, 2H, J=7, 2), 7.37 (d, 1H, J=2), 7.18 (dd, 1H, J=9, 2), 6.26 (s, 1H), 6.21 (s, 1H), 5.08 (s, 1H), 4.64 (d, 1H, J=15), 4.44 (d, 1H, J=15), 4.27 (t, 1H, J=7), 2.59 (s, 3H), 1.94–1.87 (m, 1H), 1.68 (s, 9H), 1.38–1.25 (m, 2H), 0.75 (d, 3H, J=7), 0.68 (d, 3H, J=7); MS (APCI+): 548, 550 (C$_{27}$H$_{35}$ClN$_3$O$_5$S, M++H); HRMS (ES+): Calcd for C$_{27}$H$_{34}$ClN$_3$NaO$_5$S (M++Na): 570.1802, Found: 570.1817.

EXAMPLE 4

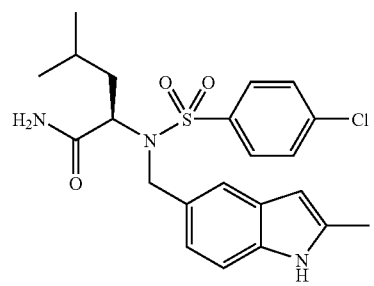

2R-(N-(2-methylindol-5-ylmethyl)-N-4-chlorophenylsulfonyl)amino-4-methyl-pentanamide. 2R-(N-(1-t-Butyloxycarbonyl-2-methylindol-5-ylmethyl)-N-4-chlorophenylsulfonyl)amino-4-methyl-pentanamide (60 mg, 0.11 mmol), TFA (1 mL) and DCM (1 mL) were stirred at room temperature for 2 h. The reaction mixture was diluted with EtOAc (20 mL), washed three times with a saturated NaHCO3 solution (10 mL) and then brine (10 mL). Drying over Na$_2$SO$_4$, filtration and concentration in vacuo provided a solid. Column chromatography (EtOAc:hexane::1:1, then EtOAc) and removal of solvent in vacuo gave the title product, an orange solid (40 mg, 82% yield): $^1$H NMR (CDCl$_3$, 300 MHz): 7.68 (dd, 2H, J=9, 2), 7.44 (d, 1H, J=2), 7.40 (dd, 2H, J=9,2), 7.19 (d, 1H, J=7), 7.09 (dd, 1H, J=7, 2), 6.17 (br s, 2H), 5.05 (br s, 1H), 4.61 (d, 1H, J=15), 4.44 (d, 1H, J=15), 4.26 (t, 1H, J=7), 2.45 (s, 3H), 1.95–1.87 (m, 1H), 1.40–1.33 (m, 2H), 0.75 (d, 3H, J=7), 0.69 (d, 3H, J=7); HRMS (ES+): Calcd for C$_{22}$H$_{26}$ClN$_3$NaO$_3$S (M++Na): 470.1281, Found: 470.1252; HPLC logP=4.21 at pH 7.0.

EXAMPLE 5

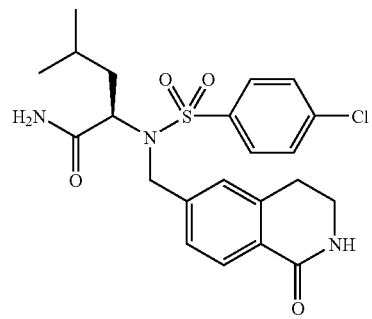

2R-(N-(1-oxo-1,2,3,4-tetrahydroisoquinolin-6-ylmethyl)-N-4-chlorophenylsulfonyl)amino-4-methyl-pentanamide. 2R-(N-(1-oxo-1,2,3,4-tetrahydroisoquinolin-6-ylmethylamino)-4-methyl-pentanamide (30 mg, 0.1 mmol), 4-chlorophenylsulfonyl chloride (25 mg, 0.12 mmol), Et$_3$N (0.28 μL, 1.38 mmol) and CH$_3$CN (2 mL) were stirred at room temperature for 20 h. The reaction mixture was diluted with EtOAc (15 mL). Successive washings were performed with a saturated Na₂CO₃ solution (10 mL), then brine (5 mL). Drying over MgSO₄, filtration and removal of solvent in vacuo gave white solid. LC-MS purification (TFA:H₂O: CH₃CN::0.5:1.0:98.5) and removal of solvent in vacuo provided a white solid (3.1 mg, 7% yield): optical purity>99% ee (HPLC (AD column, iPrOH:hexane::1:4)); ¹H NMR (CDCl₃, 300 MHz): 7.99 (d, 1H, J=7), 7.69 (dd, 2H, J=8,2), 7.47 (dd, 2H, J=8,2), 7.33 (d, 1H, J=8), 7.19 (s, 1H), 6.35 (s, 1H), 6.24 (s, 1H), 5.43 (s, 1H), 4.62 (d, 1H, J=16), 4.46 (d, 1H, J=16), 4.34 (t, 1H, J=7), 3.58–3.52 (m, 2H), 2.97–2.92 (m, 2H), 1.84–1.75 (m, 1H), 1.37–1.30 (m, 1H), 1.19–1.10 (m, 1H), 0.78 (d, 3H, J=7), 0.66 (d, 3H, J=7); HRMS (ES+): Calcd for $C_{22}H_{27}ClN_3O_4S$ (M++H): 464.1410, Found: 464.1417.

EXAMPLE 6

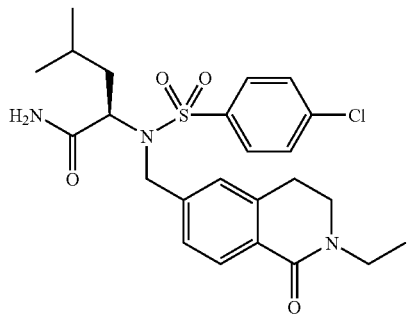

2R-(N-(1-oxo-2-ethyl-1,2,3,4-tetrahydroisoquinolin-6-ylmethylamino)-N-4-chlorophenylsulfonyl)amino-4-methyl-pentanamide. 2R-(N-(1-oxo-2-ethyl-1,2,3,4-tetrahydroisoquinolin-6-ylmethylamino)-4-methyl-pentanamide (220 mg, 0.69 mmol), 4-chlorophenylsulfonyl chloride (218 mg, 1.04 mmol), Et₃N (0.19 mL, 1.38 mmol) and DCM (2 mL) were stirred at room temperature for 20 h. The reaction mixture was diluted with EtOAc (15 mL). Successive washings were performed with water (5 mL), a 1N HCl solution (10 mL), a saturated Na₂CO₃ solution (10 mL) and brine (5 mL). Drying over MgSO4, filtration and removal of solvent in vacuo gave an oil. Column chromatography (EtOAc) and removal of solvent in vacuo provided a white solid (74 mg, 22% yield): optical purity>99% ee (HPLC (AD column, iPrOH:hexane::1:4)); ¹H NMR (DMSO-d6, 300 MHz): 7.80 (d, 2H, J=8), 7.79 (d, 1H, J=7), 7.59 (d, 2H, J=8), 7.58 (d, 1H, J=7), 7.32 (d, 1H, J=8), 7.19 (s, 1H), 7.06 (s, 1H), 4.80 (d, 1H, J=17), 4.68 (d, 1H, J=17), 4.37 (t, 1H, J=7), 3.48–3.43 (m, 4H), 2.84 (q, 2H, J=7), 1.36–1.20 (m, 3H), 1.09 (t, 3H, J=7), 0.85 (d, 3H, J=7), 0.79 (d, 3H, J=7); HRMS (ES+): Calcd for $C_{24}H_{31}ClN_3O_4S$ (M++H): 492.1724, Found: 492.1727.

EXAMPLE 7

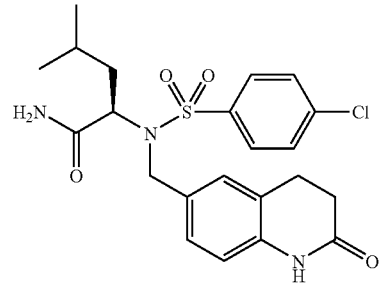

2R-(N-(2-oxo-1,2,3,4-tetrahydroquinolin-6-ylmethyl)-N-4-chlorophenylsulfonyl)amino-4-methyl-pentanamide. 2R-(N-(2-oxo-1,2,3,4-tetrahydroquinolin-6-ylmethylamino)-4-methyl-pentanamide (60 mg, 0.21 mmol), 4-chlorophenylsulfonyl chloride (48 mg, 0.23 mmol) and pyridine (2 mL) were stirred at room temperature for 16 h. The reaction mixture was diluted with EtOAc (15 mL). Successive washings were performed with water (5 mL), a 1N HCl solution (10 mL), a saturated Na₂CO₃ solution (10 mL) and brine (5 mL). Drying over MgSO₄, filtration and removal of solvent in vacuo gave an oil. Column chromatography (MeOH:DCM::3:97) and removal of solvent in vacuo provided a white solid (2.9 mg, 3% yield): ¹H NMR (CDCl₃, 300 MHz): 8.85 (s, 1H), 7.74 (dd, 2H, J=9, 2), 7.44 (dd, 2H, J=9,2), 7.25–7.18 (m, 2H), 6.7 (d, 1H, J=8), 6.57 (s, 1H), 6.38 (s, 1H), 4.65 (d, 1H, J=15), 4.26 (t, 1H, J=7), 4.24 (d, H, J=15), 2.83 (t, 2H, J=7), 2.43 (t, 2H, J=7), 1.86–1.80 (m, 1H), 1.25–1.20 (m, 1H), 1.20–1.15 (m, 1H), 0.84 (d, 3H, J=7), 0.76 (d, 3H, J=7); HRMS (ES+): Calcd for $C_{22}H_{26}ClN_3NaO_4S$ (M++Na): 486.1238, Found: 486.1249.

EXAMPLE 8

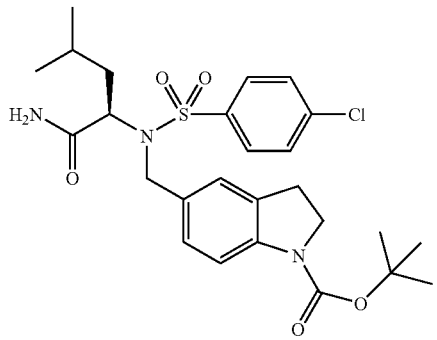

2R-(N-1-t-Butyloxycarbonylindolin-5-yl-N-4-chlorophenylsulfonyl)methylamino-4-methyl-pentanamide. D-Leucinamide (332 mg, 2.6 mmol), 1-(t-butyloxycarbonyl)-5-formylindoline (630 mg, 2.6 mmol), sodium triacetoxyborohydride (1.62 g, 7.7 mmol), HOAc (0.88 mL, 15.3 mmol) and DCE (15 mL) were reacted according to the procedure given for intermediate 2. The standard workup afforded 2R-(1-t-butyloxycarbonylindolin-5-ylmethylamino)-4-methyl-pentanamide, a white solid, which was used without further purification: ¹H NMR (CDCl₃, 300 MHz): 7.80 (br s, 1H), 7.09–7.02 (m, 3H), 5.43 (br s, 1H), 3.98 (t, 2H, J=7), 3.74 (d, 1H, J=14), 3.59 (d, 1H, J=14), 3.19–3.14 (m, 1H), 3.07 (t, 2H, J=7), 1.8–1.4 (m, 3H), 1.56 (s, 9H), 0.94 (d, 3H, J=7), 0.85 (d, 3H); MS (APCI+): 362 ($C_{20}H_{32}N_2O_3$, M++H). The above intermediate, 4-chlorophenylsulfonylchloride (807 mg, 3.82 mmol), Et3N (0.71 mL, 5.10 mmol) were reacted in DCM (10 mL) according to the procedure described for Example 1. Column chromatography (EtOAc:hexanes::2:3) followed by removal of solvent in vacuo afforded a white solid (730 mg, 53% overall yield): $^1$H NMR (CDCl$_3$, 300 MHz): 7.85 (s, 1H), 7.67 (dd, 2H, J=9, 2), 7.45 (dd, 2H, J=9,2), 7.25–7.18 (m, 2H), 6.25 (s, 1H), 5.17 (s, 1H), 4.50 (d, 1H, J=15, 4.30 (d, 1H, J=15), 4.35–4.25 (m, 1H), 3.97 (t, 2H, J=7), 3.06–2.98 (m, 2H), 1.88–1.80 (m, 1H), 1.57 (s, 9H), 1.4–1.2 (m, 2H), 0.76 (d, 3H, J=7), 0.70 (d, 3H, J=7); HRMS (ES+): Calcd for $C_{26}H_{34}ClN_3NaO_5S$ (M++Na): 558.1806, Found: 558.1787.

EXAMPLE 9

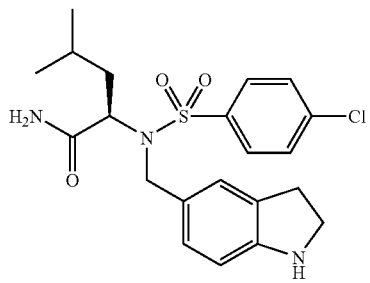

2R-(N-indolin-5-yl-N-4-chlorophenylsulfonyl)methylamino-4-methyl-pentanamide. 2R-(N-1-t-Butyloxycarbonylindolin-5-yl-N-4-chlorophenylsulfonyl)methylamino-4-methyl-pentanamide (710 mg, 1.32 mmol), TFA (2.5 mL) and DCM (2.5 mL) were stirred according to the procedure outlined for Example 2. Column chromatography (DCM: MeOH::97:3) followed by removal of solvent in vacuo afforded a white solid (528 mg, 92% overall yield): $^1$H NMR (CDCl$_3$, 300 MHz): 7.65 (dd, 2H, J=9, 2), 7.44 (dd, 2H, J=9,2), 7.05 (s, 1H), 6.95 (d, 1H, J=8), 6.52 (d, 1H, J=8), 4.42 (d, 1H, J=16), 4.43 (d, 1H, J=16), 4.45–4.35 (m, 2H), 3.78 (s, 1H), 3.56 (t, 2H, J=7), 3.06–2.96 (m, 2H), 1.88–1.80 (m, 1H), 1.4–1.25 (m, 2H), 0.76 (d, 3H, J=7), 0.70 (d, 3H, J=7); HRMS (ES+): Calcd for $C_{21}H_{26}ClN_3O_3SNa$ (M++Na): 458.1281, Found: 458.1277.

EXAMPLE 10

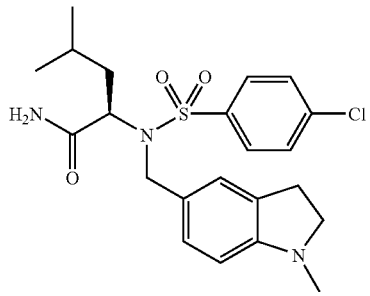

2R-(N-1-methylindolin-5-yl-N-4-chlorophenylsulfonyl)methylamino-4-methyl-pentanamide. 2R-(N-indolin-5-yl-N-4-chlorophenylsulfonyl)methylamino-4-methyl-pentanamide (44 mg, 0.1 mmol), Cs$_2$CO$_3$ (65 mg, 0.2 mmol), CH$_3$I (7 μL, 0.11 mmol) and DMF (1 mL) were mixed and stirred at 45° C. for 22 h. The reaction mixture was cooled to room temperature and diluted with EtOAc (10 mL). The organic solution was washed with a 5% LiCl solution (2×5 mL), then brine (5 mL). Drying over Na$_2$SO$_4$, filtration and removal of solvent in vacuo gave an oil. Column chromatography (EtOAc:hexane:: 1:1) and removal of solvent in vacuo gave the title product, a white solid (16 mg, 36% yield): $^1$H NMR (CDCl$_3$, 300 MHz): 7.63 (dd, 2H, J=9, 2), 7.41 (dd, 2H, J=9,2), 7.05 (s, 2H), 6.33 (d, 1H, J=8), 6.25 (s, 1H), 5.18 (s, 1H), 4.40 (d, 1H, J=16), 4.30 (d, 1H, J=16), 4.35–4.25 (m, 1H), 3.30 (t, 2H, J=7), 3.06–2.96 (m, 2H), 2.74 (s, 3H), 1.88–1.80 (m, 1H), 1.6–1.4 (m, 2H), 0.76 (d, 3H, J=7), 0.72 (d, 3H, J=7); MS (ES+): 472 ($C_{22}H_{28}ClN_3NaO_2S$, M++Na); HRMS (ES+): Calcd for $C_{22}H_{28}ClN_3O_3SNa$ (M++Na): 472.1438, Found: 472.1435.

EXAMPLE 11

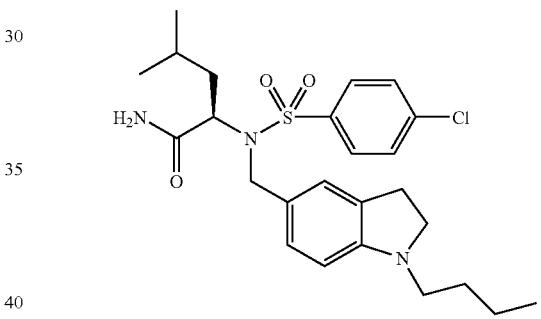

2R-(N-1-butylindolin-5-yl-N-4-chlorophenylsulfonyl)methylamino-4-methyl-pentanamide. 2R-(N-indolin-5-yl-N-4-chlorophenylsulfonyl)methylamino-4-methyl-pentanamide (44 mg, 0.1 mmol), Cs$_2$CO$_3$ (65 mg, 0.2 mmol), C$_4$H$_{71}$ (13 μL, 0.11 mmol) and DMF (1 mL) were mixed and stirred at 45° C. for 22 h. The reaction mixture was cooled to room temperature and diluted with EtOAc (10 mL). The organic solution was washed with a 5% LiCl solution (2×5 mL), then brine (5 mL). Drying over Na$_2$SO$_4$, filtration and removal of solvent in vacuo gave an oil. Column chromatography (EtOAc:hexane::2:3) and removal of solvent in vacuo gave the title product, a white solid (15 mg, 31% yield): $^1$H NMR (CDCl$_3$, 300 MHz): 7.62 (dd, 2H, J=9, 2), 7.40 (dd, 2H, J=9,2), 6.97–6.93 (m, 2H), 6.30 (d, 1H, J=8), 6.22 (s, 1H), 5.15 (s, 1H), 4.40 (d, 1H, J=16), 4.30 (d, 1H, J=16), 4.35–4.25 (m, 1H), 3.35 (t, 2H, J=7), 3.03 (t, 2H, J=7), 2.95–2.85 (m, 2H), 1.95–1.90 (m, 1H), 1.7–1.6 (m, 2H), 1.55–1.30 (m, 4H), 0.97 (t, 3H, J=7), 0.77 (d, 3H, J=7), 0.73 (d, 3H, J=7); MS (APCI+): 492, 494 ($C_{25}H_{34}ClN_3O_3S$, M++H);); HRMS (ES+): Calcd for $C_{25}H_{35}ClN_3O_3S$ (M++H): 492.2088, Found: 492.2082.

EXAMPLE 12

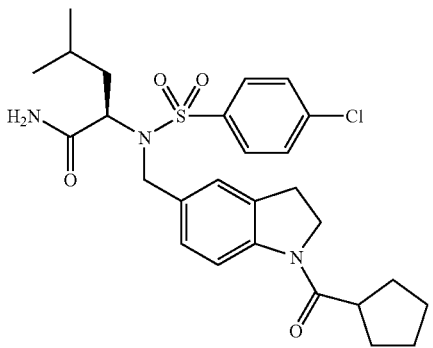

2R-(N-1-cyclopentylcarbonylindolin-5-yl-N-4-chlorophenylsulfonyl)methylamino-4-methyl-pentanamide. 2R-(N-indolin-5-yl-N-4-chlorophenylsulfonyl)methylamino-4-methyl-pentanamide (44 mg, 0.1 mmol), cyclopentylcarbonyl chloride (13 mg, 0.1 mmol), Et$_3$N (21 µL, 0.15 mmol), 4-dimethylaminopyridine (12 mg, 0.1 mmol) and DCM (1 mL) were mixed and stirred at 25° C. for 4 h. The reaction mixture was diluted with water (5 mL) and extracted with EtOAc (3×10 mL). The combined organic layers were washed with brine (5 mL). Drying over Na$_2$SO$_4$, filtration and removal of solvent in vacuo gave an oil. Column chromatography (EtOAc:hexane:: 1:1) and removal of solvent in vacuo gave the title product, a white solid (53 mg, 100% yield): $^1$H NMR (CDCl$_3$, 300 MHz): 8.18 (d, 1H), 7.66 (dd, 2H, J=9, 2), 7.45 (dd, 2H, J=9,2), 7.15–7.11 (m, 2H), 6.25 (s, 1H), 5.19 (s, 1H), 4.33 (d, 1H, J=16), 4.23 (d, 1H, J=16), 4.35–4.25 (m, 1H), 4.14 (t, 2H, J=7), 3.2–3.15 (m, 2H), 3.00–2.96 (m, 1H), 2.10–1.7 (m, 8H), 1.45–1.20 (m, 3H), 0.75 (d, 3H, J=7), 0.69 (d, 3H, J=7); MS (ES+): 554 (C$_{27}$H$_{34}$ClN$_3$NaO$_4$S, M++Na).

EXAMPLES 13 THROUGH 20

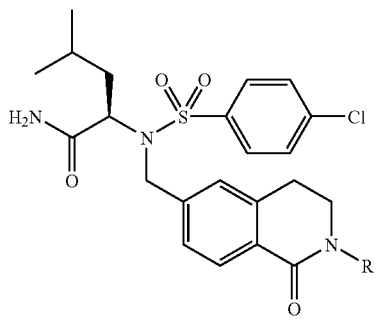

(13) R = Me
(14) R = Pr
(15) R = Bu
(16) R = CH$_2$Ph
(17) R = CH$_2$CH$_2$OMe
(18) R = CH$_2$-cyclopropyl
(19) R = CH$_2$-cyclobutyl
(20) R = CH$_2$-(2-pyridyl)

Following the procedures described in example 6, the following compounds were prepared from the appropriate (1,2,3,4-tetrahydroisoquinolin-6-ylmethylamino) pentanamide and 4-chlorobenzenesulfonyl chloride then purified by column chromatography (EtOAc: hexanes::1:3 to 1:1):

EXAMPLE 13

2R-(N-(1-oxo-2-(2-pyridylmethyl)-1,2,3,4-tetrahydroisoquinolin-6-ylmethylamino)-N-4-chlorophenylsulonyl)amino-4-methyl-pentanamide. 3.5 mg (pale yellow oil, 5% yield); $^1$H NMR (CDCl$_3$, 300 MHz): 8.84 (d, 1H, J=8), 8.27 (t, 1H, J=8), 7.98 (t, 2H, J=8), 8.75–8.70 (m, 1H), 7.73 (d, 2H, J=8), 7.48 (d, 2H, J=8), 7.33 (d, 1H, J=7), 7.18 (s, 1H), 6.40 (s, 1H), 5.92 (s, 1H), 5.11 (s, 2H), 4.67 (d, 1H, J=16), 4.38 (d, 1H, J=16), 4.37–4.32 (m, 1H), 3.77 (t, 2H, J=7), 3.04 (t, 2H, J=7), 1.82 (quintet, 1H, J=7), 1.38–1.30 (m, 1H), 1.17–1.06 (m, 1H), 0.77 (d, 3H, J=7), 0.68(d, 3H, J=7); MS (ES+): 555, 557 (C$_{28}$H$_{32}$ClN$_4$O$_4$S, M++H); HRMS (ES+): Calcd for C$_{27}$H$_{35}$ClN$_3$O$_4$S (M++H): 555.1833, Found: 555.1816.

EXAMPLE 14

2R-(N-(1-oxo-2-methyl-1,2,3,4-tetrahydroisoquinolin-6-ylmethylamino)-N-4-chlorophenylsulfonyl)amino-4-methyl-pentanamide. 5.7 mg (pale yellow oil, 12% yield); $^1$H NMR (CDCl$_3$, 300 MHz): 7.97 (d, 1H, J=8), 7.72 (dd, 2H, J=8, 2), 7.49 (dd, 2H, J=8,2), 7.31 (d, 1H, J=8), 7.17 (s, 1H), 6.53 (br s, 1H), 6.47 (br s, 1H), 4.66 (d, 1H, J=16), 4.37 (d, 1H, J=16), 4.34 (t, 1H, J=6), 3.59 (t, 2H, J=7), 3.19 (s, 3H), 3.05–2.95 (m, 2H), 1.81 (quintet, 1H, J=7), 1.28 (quintet, 1H, J=7), 1.18 (quintet, 1H, J=7), 0.76 (d, 3H, J=7), 0.67 (d, 3H, J=7); MS (ES+): 478, 480 (C$_{23}$H$_{29}$ClN$_3$O$_4$S, M++H); HRMS (ES+): Calcd for C$_{23}$H$_{29}$ClN$_3$O$_4$S (M++H): 478.1567, Found: 478.1590.

EXAMPLE 15

2R-(N-(1-oxo-2-propyl-1,2,3,4-tetrahydroisoquinolin-6-ylmethylamino)-N-4-chlorophenylsulfonyl)amino-4-methyl-pentanamide. 10.7 mg (pale yellow oil, 21% yield); $^1$H NMR (CDCl$_3$, 300 MHz): 7.98 (d, 1H, J=8), 7.70 (dd, 2H, J=8, 2), 7.48 (dd, 2H, J=8,2), 7.30(d, 1H, J=8), 7.17(s, 1H), 6.36(br s, 1H), 5.69(br s, 1H), 4.61 (d, 1H, J=16), 4.43(d, 1H, J=16), 4.34(t, 1H, J=6), 3.56–3.51 (m, 4H), 3.05–2.95 (m, 2H), 1.85–1.65 (m, 4H), 1.45–1.35 (m, 1H), 0.99 (t, 3H, J=7), 0.77 (d, 3H, J=7), 0.67 (d, 3H, J=7); MS (ES+): 506, 508 (C$_{25}$H$_{33}$ClN$_3$O$_4$S, M++H); HRMS (ES+): Calcd for C$_{25}$H$_{33}$ClN$_3$O$_4$S (M++H): 506.1890, Found: 506.1879.

EXAMPLE 16

2R-(N-(1-oxo-2-butyl-1,2,3,4-tetrahydroisoquinolin-6-ylmethylamino)-N-4-chlorophenylsulfonyl)amino-4-methyl-pentanamide. 11.5 mg (pale yellow oil, 22% yield); $^1$H NMR (CDCl$_3$, 300 MHz): 7.99 (d, 1H, J=8), 7.67 (dd, 2H, J=8, 2), 7.46 (dd, 2H, J=8,2), 7.29 (d, 1H, J=8), 7.17 (s, 1H), 6.30 (br s, 1H), 5.41 (br s, 1H), 4.61 (d, 1H, J=16), 4.43 (d, 1H, J=16), 4.34 (t, 1H, J=6), 3.65–3.51 (m, 4H), 3.00–2.90 (m, 2H), 1.83 (quintet, 1H, J=7), 1.77–1.71 (m, 2H), 1.50–1.30 (m, 3H), 1.23–1.16 (m, 1H), 0.96 (t, 3H, J=7), 0.77 (d, 3H, J=7), 0.67(d, 3H, J=7); MS (ES+): 520, 522 (C$_{26}$H$_{35}$ClN$_3$O$_4$S, M++H); HRMS (ES+): Calcd for C$_{26}$H$_{35}$ClN$_3$O$_4$S (M++H): 520.2037, Found: 520.2017.

EXAMPLE 17

2R-(N-(1-oxo-2-benzyl-1,2,3,4-tetrahydroisoquinolin-6-ylmethylamino)-N-4-chlorophenylsulfonyl)amino-4-methyl-pentanamide. 6.4 mg (pale yellow oil, 12% yield); $^1$H NMR (CDCl$_3$, 300 MHz): 8.09 (d, 1H, J=8), 7.75 (dd, 2H, J=8, 2), 7.50 (dd, 2H, J=8,2), 7.46–7.30 (m, 6H), 7.17 (s, 1H), 7.07–6.94 (m, 2H), 4.82 (d, 1H, J=8), 4.78 (d, 1H, J=8), 4.61 (d, 1H, J=16), 4.44 (t, 1H, J=6), 4.33 (d, 1H, J=16), 3.53 (t, 2H, J=7), 3.10–2.94 (m, 2H), 1.82 (quintet, 1H, J=7), 1.40–1.35 (m, 1H), 1.23–1.16 (m, 1H), 0.77 (d, 3H, J=7), 0.67(d, 3H, J=7); MS (ES+): 554, 556 (C$_{29}$H$_{33}$ClN$_3$O$_4$S, M++H).

EXAMPLE 18

2R-(N-(1-oxo-2-(2-methoxyethyl)-1,2,3,4-tetrahydroisoquinolin-6-ylmethylamino)-N-4-chlorophenylsulonyl)amino-4-methyl-pentanamide. 8.5 mg (pale yellow oil, 16% yield); $^1$H NMR (CDCl$_3$, 300 MHz): 7.96 (d, 1H, J=8), 7.70 (dd, 2H, J=8, 2), 7.49 (dd, 2H, J=8,2), 7.30 (d, 1H, J=8), 7.16 (s, 1H), 6.49 (br s, 1H), 6.26 (br s, 1H), 4.65 (d, 1H, J=16), 4.38 (d, 1H, J=16), 4.35 (t, 1H, J=6), 3.85–3.76 (m, 2H), 3.70–3.55 (m, 4H), 3.37 (s, 3H), 3.03–2.92 (m, 2H), 1.82 (quintet, 1H, J=7), 1.45–1.46 (m 1H), 1.25–1.12 (m, 1H), 0.77 (d, 3H, J=7), 0.68(d, 3H, J=7); MS (ES+): 522, 524 (C$_{25}$H$_{33}$ClN$_3$O$_5$S, M++H); HRMS (ES+): Calcd for C$_{25}$H$_{33}$ClN$_3$O$_5$S (M++H): 522.1829, Found: 522.1841.

EXAMPLE 19

2R-(N-(1-oxo-2-cyclopropylmethyl-1,2,3,4-tetrahydroisoquinolin-6-ylmethylamino)-N-4-chlorophenylsulfonyl)amino-4-methyl-pentanamide. 11.6 mg (pale yellow oil, 22% yield); $^1$H NMR (CDCl$_3$, 300 MHz): 7.99 (d, 1H, J=8), 7.85–7.70 (m, 1H), 7.73 (dd, 2H, J=8, 2), 7.50 (dd, 2H, J=8,2), 7.36 (d, 1H, J=8), 7.17 (s, 1H), 6.77 (br s, 1H), 4.74 (d, 1H, J=16), 4.33 (d, 1H, J=16), 4.35 (t, 1H, J=6), 3.70 (t, 2H, J=7), 3.52 (d, 2H, J=7), 3.02 (t, 2H, J=7), 1.82 (quintet, 1H, J=7), 1.40–1.25 (m, 1H), 1.22–1.08 (m, 2H), 0.76 (d, 3H, J=7), 0.69(d, 3H, J=7), 0.69–0.59 (m, 2H), 0.37–0.30 (m, 2H); MS (ES+): 518, 520 (C$_{26}$H$_{33}$ClN$_3$O$_4$S, M++H);

EXAMPLE 20

2R-(N-(1-oxo-2-cyclobutylmethyl-1,2,3,4-tetrahydroisoquinolin-6-ylmethylamino)-N-4-chlorophenylsulfonyl)amino-4-methyl-pentanamide. 10.8 mg (pale yellow oil, 20% yield); $^1$H NMR (CDCl$_3$, 300 MHz): 7.97 (d, 1H, J=8), 7.68 (dd, 2H, J=8, 2), 7.47 (dd, 2H, J=8,2), 7.28 (d, 1H, J=8), 7.13 (s, 1H), 6.77 (br s, 1H), 5.80 (br s, 1H), 4.74 (d, 1H, J=16), 4.33 (d, 1H, J=16), 4.35 (t, 1H, J=6), 3.61 (d, 2H, J=7), 3.52 (t, 2H, J=7), 2.98 (t, 2H, J=7), 2.67 (quintet, 1H, J=7), 2.25–2.05 (m, 2H), 1.92–1.68 (m, 4H), 1.43–1.26 (m, 1H), 1.15 (quintet, 1H, J=7), 0.98–0.86 (m, 1H), 0.76 (d, 3H, J=7), 0.69(d, 3H, J=7); MS (ES+): 532, 534 (C$_{27}$H$_{35}$ClN$_3$O$_4$S, M++H); HRMS (ES+): Calcd for C$_{27}$H$_{35}$ClN$_3$O$_4$S (M++H): 532.2037, Found: 532.2060.

EXAMPLE 21

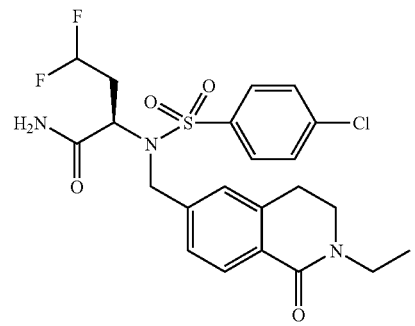

2R-(N-(1-oxo-2-ethyl-1,2,3,4-tetrahydroisoquinolin-6-ylmethylamino)-N-4-chlorophenylsulfonyl)amino-3-cyclopropyl-propanamide. 2R-(4-chlorophenylsulfonyl)amino-3-cyclopropyl-propanamide (91 mg, 0.3 mmol), 2-ethyl-5-methanesulfonyloxymethyl-2H-1,2,3,4-tetrahydroisoquinolone (85 mg, 0.3 mmol), Cs$_2$CO$_3$ (195 mg, 0.6 mmol) and DMF (2 mL) were stirred at ambient temperature for 16 h under a nitrogen atmosphere. The reaction mixture was diluted twentyfold with EtOAc and the resulting solution was washed three times with a 10% LiCl solution (5 mL), then once with brine (5 mL). The organic solution was dried over MgSO$_4$, filtered and concentrated in vacuo. Column chromatography (EtOAc:hexane::4:1) of the residue and removal of solvent from the fractions afforded a white solid (100 mg, 68% yield): $^1$H NMR (CDCl$_3$, 300 MHz): 8.01 (d, 1H, J=8), 7.69 (d, 2H, J=8), 7.45 (d, 2H, J=8), 7.32 (d, 1H, J=8, 7.13 (s, 1H), 6.33 (s, 1H), 5.19 (s, 1H), 4.64 (d, 1H, J=16), 4.40 (d, 1H, J=16), 4.33 (t, 1H, J=7), 3.62 (q, 2H, J=7), 3.55 (t, 2H, J=7), 2.99–2.93 (m, 2H), 1.85–1.78 (m, 1H), 1.39–1.33 (m, 1H), 1.25 (t, 3H, J=7), 0.4–0.33 (m, 2H), 0.28–0.19 (m, 1H), 0.02 to –0.09 (m, 1H), –0.1 to –0.2 (m, 1H); MS (APCI+): 490 (C$_{24}$H$_{29}$ClN$_3$O$_4$S, M++H); HRMS (ES+): Calcd for C$_{24}$H$_{29}$ClN$_3$O$_4$S (M++H): 490.1567, Found: 490.1582.

EXAMPLE 22

2R-(N-(1-oxo-2-ethyl-1,2,3,4-tetrahydroisoquinolin-6-ylmethylamino)-N-4-chlorophenylsulfonyl)amino-4,4-difluorobutanamide. 2R-(4-chlorophenylsulfonyl)amino-4,4-difluorobutanamide (100 mg, 0.32 mmol), 2-ethyl-5-methanesulfonyloxymethyl-2H-1,2,3,4-tetrahydroisoquinolone (91 mg, 0.32 mmol), Cs$_2$CO$_3$ (209 mg, 0.64 mmol), KI (106 mg, 0.64 mmol) and DMF (2 mL) were stirred at ambient temperature for 48 h under a nitrogen atmosphere. The reaction mixture was diluted twentyfold with EtOAc and the resulting solution was washed three times with a 10% LiCl solution (5 mL), then once with brine (5 mL). The organic solution was dried over MgSO$_4$, filtered and concentrated in vacuo. Column chromatography (EtOAc:hexane::4:1) of the residue and removal of solvent from the fractions afforded a white solid (84 mg, 53% yield): $^1$H NMR (CDCl$_3$, 300 MHz): 8.02 (d, 1H, J=8), 7.73 (d, 2H, J=8), 7.53 (d, 2H, J=8), 7.28 (d, 1H, J=8), 7.07 (s, 1H), 6.33 (s, 1H), 5.75 (br t, 1H, J=8), 5.22 (s, 1H), 4.60–4.55 (m, 1H), 4.55 (d, 1H, J=16), 4.33 (d, 1H, J=16), 3.62 (q, 2H, J=7), 3.55 (t, 2H, J=7), 2.99–2.93 (m, 2H), 2.68–2.50 (m, 2H), 1.57–1.50 (m, 1H), 1.23 (t, 3H, J=7); MS (APCI+): 500 (C$_{22}$H$_{25}$ClF$_2$N$_3$O$_4$S, M++H); HRMS (ES+): Calcd for C$_{22}$H$_{25}$ClF$_2$N$_3$O$_4$S (M++H): 500.1222, Found: 500.1212.

EXAMPLES 23 AND 24

(23) R = 2-propyl
(24) R = 3-pentyl

Following the procedure described in example 21, the following compounds were prepared from the appropriate methanesulfonate and sulfonamide:

EXAMPLE 23

2R-(N-(1-oxo-2-(2-propyl)-1,2,3,4-tetrahydroisoquinolin-6-ylmethylamino)-N-4-chlorophenylsulfonyl)amino-3-cyclopropyl-propanamide. 306 mg (35% yield): $^1$H NMR (CDCl$_3$, 300 MHz): 8.00 (d, 1H, J=8), 7.69 (d, 2H, J=8), 7.44 (d, 2H, J=8), 7.31 (d, 1H, J=8), 7.12 (s, 1H), 6.32 (s, 1H), 5.19 (s, 1H), 5.07 (septet, 1H, J=7), 4.63 (d, 1H, J=16), 4.36 (d, 1H, J=16), 4.33 (t, 1H, J=7), 3.40 (t, 2H, J=7), 2.87 (m, 2H), 1.74 (m, 1H), 1.28 (m, 1H), 1.19 (d, 6H, J=7), 0.31 (m, 2H), 0.19 (m, 1H), –0.05 (m, 1H), –0.14 (m, 1H); HRMS (ES+): Calcd for C$_{25}$H$_{31}$ClN$_3$O$_4$S: 504.1724 (M++H), Found: 504.1740.

EXAMPLE 24

2R-(N-(1-oxo-2-(3-pentyl)-1,2,3,4-tetrahydroisoquinolin-6-ylmethylamino)-N-4-chlorophenylsulfonyl)amino-3-cyclopropyl-propanamide. 407 mg (54% yield): $^1$H NMR (CDCl$_3$, 300 MHz): 8.02 (d, 1H, J=8), 7.69 (d, 2H, J=8), 7.44 (d, 2H, J=8), 7.31 (d, 1H, J=8), 7.12 (s, 1H), 6.32 (s, 1H), 5.20 (s, 1H), 4.62 (quintet, 1H, J=7), 4.61 (d, 1H, J=16), 4.42 (d, 1H, J=16), 4.36 (t, 1H, J=7), 3.31 (t, 2H, J=7), 2.89 (m, 2H), 1.76 (m, 1H), 1.53 (m, 6H), 1.48 (m, 2H), 0.90 (t, 3H, J=7), 0.31 (m, 2H), 0.19 (m, 1H), –0.05 (m, 1H), –0.14 (m, 1H); HRMS (ES+): Calcd for C$_{27}$H$_{35}$ClN$_3$O$_4$S: 532.2037 (M++H), Found: 532.2039.

I claim:

1. A compound of Formula I wherein:

Ar$^1$ is

Ar$^2$ is

R$^1$ is C$_{1-6}$alkyl, (C$_{3-7}$cycloalkyl)C$_{1-6}$alkyl, or C$_{1-6}$fluoroalkyl;

R$^2$ is hydrogen, C$_{1-6}$alkyl, (C$_{3-7}$cycloalkyl)C$_{1-6}$alkyl, (phenyl)C$_{1-6}$alkyl, (pyridinyl)C$_{1-6}$alkyl, (C$_{1-6}$alkoxy)C$_{1-6}$alkyl, COR$^4$, or CO$_2$R$^4$;

R$^3$ is hydrogen or C$_{1-6}$alkyl;

R$^4$ is C$_{1-6}$alkyl, or C$_{3-7}$cycloalkyl;

R$^5$ is halogen; and

R$^6$ is hydrogen or halogen;

or a pharmaceutically acceptable salt or solvate thereof.

2. A compound of claim 1 where Ar$^1$ is

3. A compound of claim 2 where Ar¹ is

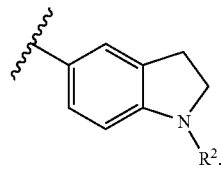

4. A compound of claim 1 where Ar¹ is

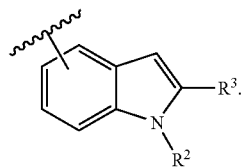

5. A compound of claim 4 where Ar¹ is

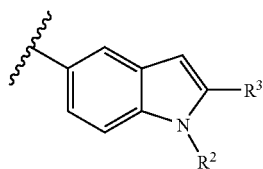

and R³ is hydrogen or methyl.

6. A compound of claim 1 where Ar¹ is

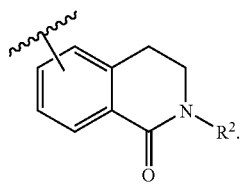

7. A compound of claim 6 where Ar¹ is

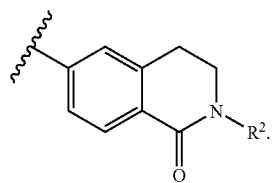

8. A compound of claim 1 where Ar¹ is

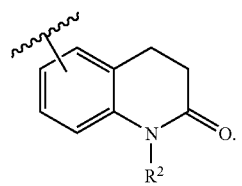

9. A compound of claim 8 where Ar¹ is

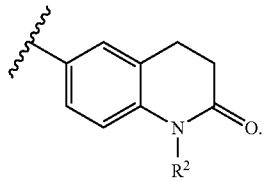

10. A compound of claim 1 where Ar² is 4-chlorophenyl.

11. A compound of claim 1 where R¹ is selected from the group consisting of n-propyl, i-propyl, n-butyl, s-butyl, i-butyl, t-butyl, difluoroethyl, trifluoropropyl, and cyclopropylmethyl.

12. A compound of claim 1 where R² is selected from the group consisting of hydrogen, methyl, ethyl, n-propyl, i-propyl, n-butyl, s-butyl, i-butyl, t-butyl, cyclopropylmethyl, cyclobutylmethyl, methoxyethyl, cyclopentylcarbonyl, butyloxycarbonyl, benzyl, and pyridinylmethyl.

13. A compound of claim 1 according to Formula Ia.

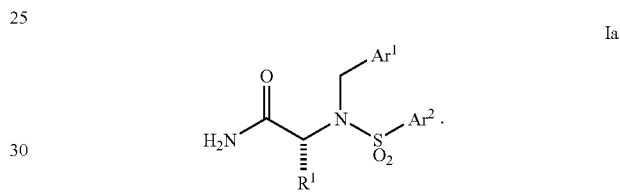

14. A compound of claim 1 selected from the group consisting of 2R-(N-1-t-butyloxycarbonylindol-5-ylmethyl-N-4-chlorophenylsulfonylamino)-4-methyl-pentanamide;

2R-(N-indol-5-ylmethyl-N-4-chlorophenylsulfonyl)amino-4-methyl-pentanamide;

2R-(1-t-Butyloxycarbonyl-2-methylindol-5-ylmethylamino)-4-methyl-pentanamide;

2R-(N-(1-t-Butyloxycarbonyl-2-methylindol-5-ylmethyl)-N-4-chlorophenylsulfonyl)amino-4-methyl-pentanamide;

2R-(N-(2-methylindol-5-ylmethyl)-N-4-chlorophenylsulfonyl)amino-4-methyl-pentanamide;

2R-(N-(1-oxo-1,2,3,4-tetrahydroisoquinolin-6-ylmethyl)-N-4-chlorophenylsulfonyl)amino-4-methyl-pentanamide;

2R-(N-(1-oxo-2-ethyl-1,2,3,4-tetrahydroisoquinolin-6-ylmethylamino)-N-4-chlorophenylsulfonyl)amino-4-methyl-pentanamide;

2R-(N-(2-oxo-1,2,3,4-tetrahydroquinolin-6-ylmethyl)-N-4-chlorophenylsulfonyl)amino-4-methyl-pentanamide;

2R-(N-1-t-Butyloxycarbonylindolin-5-yl-N-4-chlorophenylsulfonyl)methylamino-4-methyl-pentanamide;

2R-(N-indolin-5-yl-N-4-chlorophenylsulfonyl)methylamino-4-methyl-pentanamide;

2R-(N-1-methylindolin-5-yl-N-4-chlorophenylsulfonyl)methylamino-4-methyl-pentanamide;

2R-(N-1-butylindolin-5-yl-N-4-chlorophenylsulfonyl)methylamino-4-methyl-pentanamide;

2R-(N-1-cyclopentylcarbonylindolin-5-yl-N-4-chlorophenylsulfonyl)methylamino-4-methyl-pentanamide;

2R-(N-(1-oxo-2-methyl-1,2,3,4-tetrahydroisoquinolin-6-ylmethylamino)-N-4-chlorophenylsulfonyl)amino-4-methyl-pentanamide;

2R-(N-(1-oxo-2-propyl-1,2,3,4-tetrahydroisoquinolin-6-ylmethylamino)-N-4-chlorophenylsulfonyl)amino-4-methyl-pentanamide;

2R-(N-(1-oxo-2-butyl-1,2,3,4-tetrahydroisoquinolin-6-ylmethylamino)-N-4-chlorophenylsulfonyl)amino-4-methyl-pentanamide;

2R-(N-(1-oxo-2-benzyl-1,2,3,4-tetrahydroisoquinolin-6-ylmethylamino)-N-4-chlorophenylsulfonyl)amino-4-methyl-pentanamide;

2R-(N-(1-oxo-2-(2-methoxyethyl)-1,2,3,4-tetrahydroisoquinolin-6-ylmethylamino)-N-4-chlorophenylsulfonyl)amino-4-methyl-pentanamide;

2R-(N-(1-oxo-2-cyclopropylmethyl-1,2,3,4-tetrahydroisoquinolin-6-ylmethylamino)-N-4-chlorophenylsulfonyl)amino-4-methyl-pentanamide;

2R-(N-(1-oxo-2-cyclobutylmethyl-1,2,3,4-tetrahydroisoquinolin-6-ylmethylamino)-N-4-chlorophenylsulfonyl)amino-4-methyl-pentanamide;

2R-(N-(1-oxo-2-(2-pyridylmethyl)-1,2,3,4-tetrahydroisoquinolin-6-ylmethylamino)-N-4-chlorophenylsulfonyl)amino-4-methyl-pentanamide;

2R-(N-(1-oxo-2-ethyl-1,2,3,4-tetrahydroisoquinolin-6-ylmethylamino)-N-4-chlorophenylsulfonyl)amino-3-cyclopropyl-propanamide;

2R-(N-(1-oxo-2-ethyl-1,2,3,4-tetrahydroisoquinolin-6-ylmethylamino)-N-4-chlorophenylsulfonyl)amino-4,4-difluorobutanamide;

2R-(N-(1-oxo-2-(2-propyl)-1,2,3,4-tetrahydroisoquinolin-6-ylmethylamino)-N-4-chlorophenylsulfonyl)amino-3-cyclopropyl-propanamide; and 2R-(N-(1-oxo-2-(3-pentyl)-1,2,3,4-tetrahydroisoquinolin-6-ylmethylamino)-N-4-chlorophenylsulfonyl)amino-3-cyclopropyl-propanamide;

or a pharmaceutically acceptable salt or solvate thereof.

15. A composition for the treatment of Alzheimer's or Down's Syndrome comprising a therapeutically effective amount of a compound of claim 1 and a pharmaceutically acceptable carrier or diluent.

16. A method for the treatment of Alzheimer's disease or Down's Syndrome comprising a therapeutically effective amount of a compound of claim 1 and a pharamaceutically acceptable carrier or diluent.

* * * * *

UNITED STATES PATENT AND TRADEMARK OFFICE
CERTIFICATE OF CORRECTION

PATENT NO.       : 7,144,894 B2
APPLICATION NO.  : 11/231410
DATED            : December 5, 2006
INVENTOR(S)      : Paul J. Gilligan It is certified that error appears in the above-identified patent and that said Letters Patent is hereby corrected as shown below:

On column 2, line 45 and column 40, line 30

 should be

Signed and Sealed this

Twenty-ninth Day of January, 2008

JON W. DUDAS
*Director of the United States Patent and Trademark Office*